US012569236B2

(12) United States Patent
Douglas et al.

(10) Patent No.: US 12,569,236 B2
(45) Date of Patent: Mar. 10, 2026

(54) DEVICES, SYSTEMS, AND METHODS FOR INSERTING AND REMOVING SURGICAL WIRES

(71) Applicant: NuVasive, Inc., San Diego, CA (US)

(72) Inventors: Cole Douglas, San Diego, CA (US); Kelli Lynch, San Diego, CA (US); Juan Uribe, Tampa, FL (US); Shane Fedon, Elfin Forest, CA (US); Byron Riemhofer, San Diego, CA (US); Michael Serra, San Diego, CA (US); Alejandro De La Rosa, National City, CA (US); Ross Volpe, San Diego, CA (US); Chunqing Lu, San Diego, CA (US); Stephen Laffoon, San Diego, CA (US)

(73) Assignee: Nuvasive, Inc., San Diego, CA (US)

( * ) Notice: Subject to any disclaimer, the term of this patent is extended or adjusted under 35 U.S.C. 154(b) by 0 days.

(21) Appl. No.: 18/174,433

(22) Filed: Feb. 24, 2023

(65) Prior Publication Data

US 2023/0270428 A1 Aug. 31, 2023

Related U.S. Application Data

(60) Provisional application No. 63/313,841, filed on Feb. 25, 2022, provisional application No. 63/313,809, filed on Feb. 25, 2022.

(51) Int. Cl.
*A61B 17/02* (2006.01)
*A61F 2/44* (2006.01)

(52) U.S. Cl.
CPC ........ *A61B 17/0206* (2013.01); *A61F 2/4455* (2013.01)

(58) Field of Classification Search
CPC ............... A61B 17/0206; A61B 17/02; A61B 2017/0243; A61B 17/0218; A61B 17/025; A61B 2017/0256; A61B 2017/0262; A61F 2/4455
See application file for complete search history.

(56) References Cited

U.S. PATENT DOCUMENTS

| | | | | |
|---|---|---|---|---|
| 4,562,832 A | * | 1/1986 | Wilder | A61B 90/30 |
| | | | | 362/582 |
| 8,137,284 B2 | * | 3/2012 | Miles | A61B 17/3421 |
| | | | | 606/32 |
| 9,259,213 B1 | * | 2/2016 | O'Hara | A61B 17/025 |
| 11,457,910 B1 | * | 10/2022 | Lynch | A61B 17/025 |

(Continued)

*Primary Examiner* — Eduardo C Robert
*Assistant Examiner* — Holly Joanna Lane

(57) ABSTRACT

A surgical wire is part of a system that includes a retractor blade defining one or more paths for the surgical wire to follow. The paths can be one or more openings, cannulations, paths, tubes, other structures, or combinations thereof. The surgical wire can be routed through the front, back, and/or middle of the retractor blade and into a vertebral body. The surgical wire can be routed through a shim in communication with the retractor blade and into a vertebral body Systems and methods are used to insert surgical wires into bone. Systems and methods are used for removing surgical wires from bone. Systems include those for gripping and pulling or pushing surgical wires. Systems include those that interact with a retractor (e.g., an arm, body, or blade thereof) to facilitate removal of the surgical wire.

13 Claims, 28 Drawing Sheets

(56)                    References Cited

U.S. PATENT DOCUMENTS

| | | | |
|---|---|---|---|
| 2002/0138085 A1* | 9/2002 | Muramatsu | A61B 17/1227 |
| | | | 606/139 |
| 2003/0060685 A1* | 3/2003 | Houser | A61B 17/0218 |
| | | | 600/206 |
| 2005/0277812 A1* | 12/2005 | Myles | A61B 17/0293 |
| | | | 600/233 |
| 2007/0038216 A1* | 2/2007 | Hamada | A61B 17/02 |
| | | | 606/53 |
| 2007/0129608 A1* | 6/2007 | Sandhu | A61B 17/3423 |
| | | | 600/219 |
| 2008/0221394 A1* | 9/2008 | Melkent | A61B 17/0206 |
| | | | 600/219 |
| 2013/0190575 A1* | 7/2013 | Mast | A61B 17/0206 |
| | | | 600/219 |
| 2022/0104854 A1* | 4/2022 | Baynham | A61B 17/7053 |

* cited by examiner

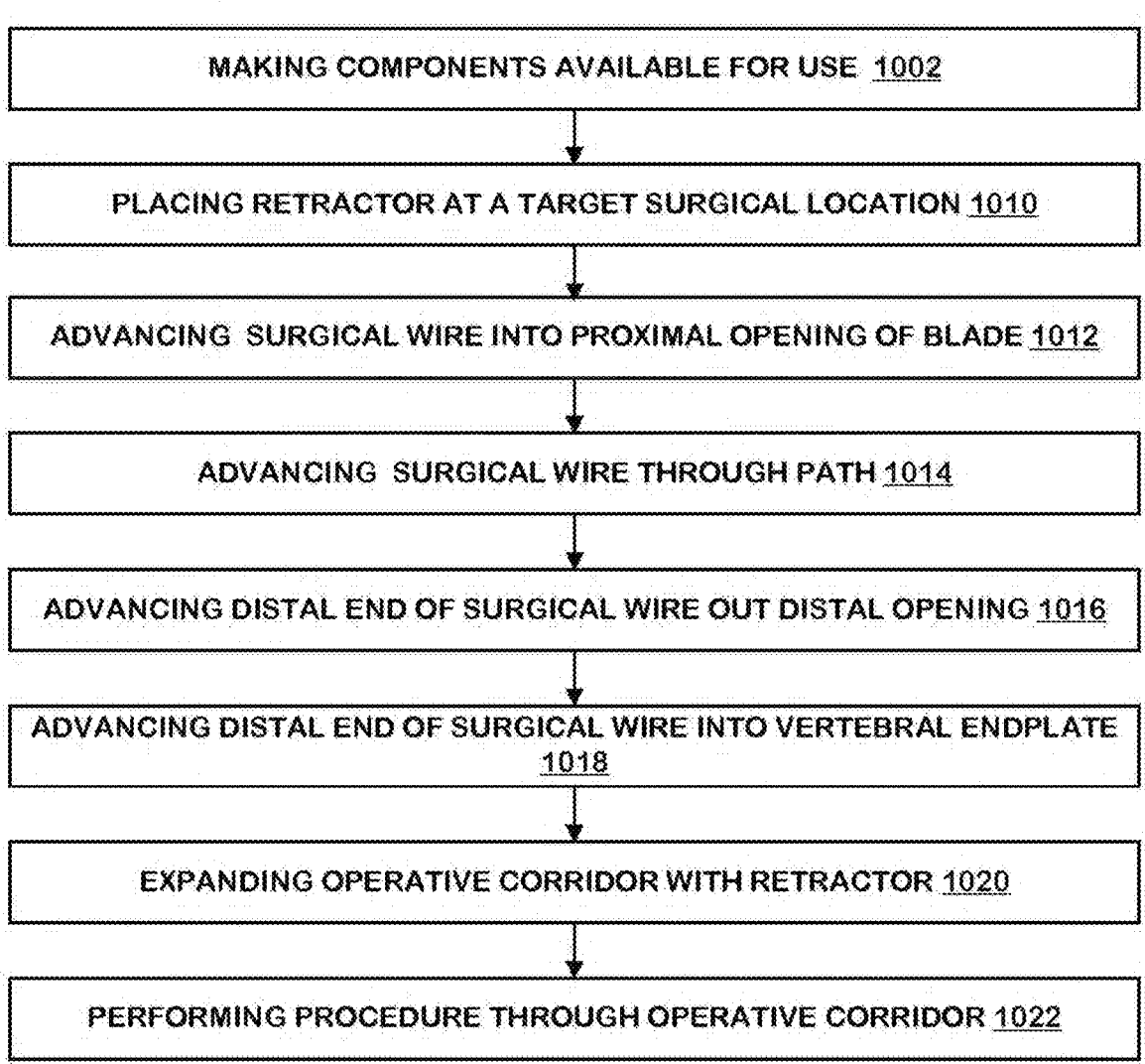

1000

MAKING COMPONENTS AVAILABLE FOR USE  1002

PLACING RETRACTOR AT A TARGET SURGICAL LOCATION 1010

ADVANCING  SURGICAL WIRE INTO PROXIMAL OPENING OF BLADE 1012

ADVANCING  SURGICAL WIRE THROUGH PATH 1014

ADVANCING DISTAL END OF SURGICAL WIRE OUT DISTAL OPENING 1016

ADVANCING DISTAL END OF SURGICAL WIRE INTO VERTEBRAL ENDPLATE 1018

EXPANDING OPERATIVE CORRIDOR WITH RETRACTOR 1020

PERFORMING PROCEDURE THROUGH OPERATIVE CORRIDOR 1022

FIG. 10

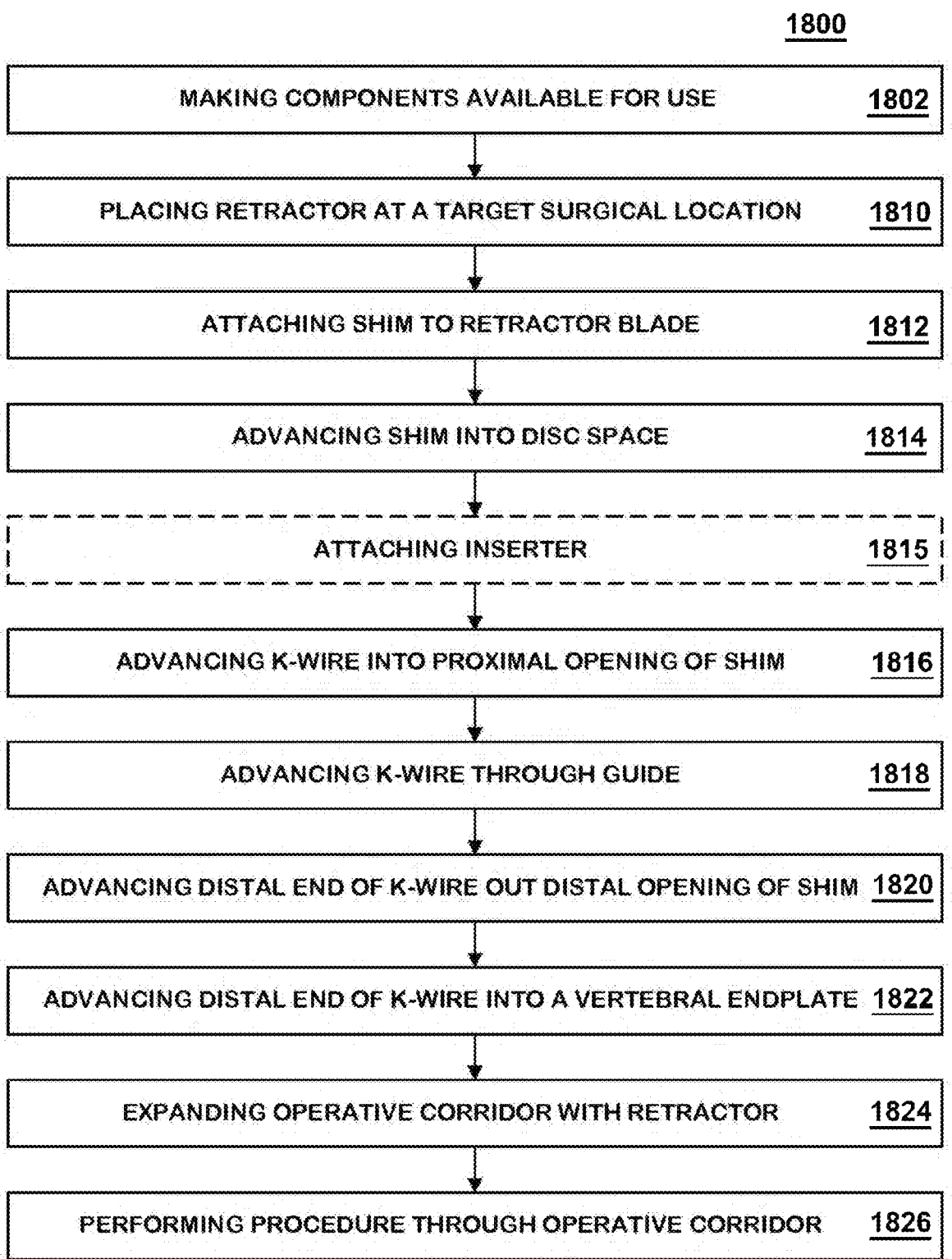

1800

| MAKING COMPONENTS AVAILABLE FOR USE | 1802 |

| PLACING RETRACTOR AT A TARGET SURGICAL LOCATION | 1810 |

| ATTACHING SHIM TO RETRACTOR BLADE | 1812 |

| ADVANCING SHIM INTO DISC SPACE | 1814 |

| ATTACHING INSERTER | 1815 |

| ADVANCING K-WIRE INTO PROXIMAL OPENING OF SHIM | 1816 |

| ADVANCING K-WIRE THROUGH GUIDE | 1818 |

| ADVANCING DISTAL END OF K-WIRE OUT DISTAL OPENING OF SHIM | 1820 |

| ADVANCING DISTAL END OF K-WIRE INTO A VERTEBRAL ENDPLATE | 1822 |

| EXPANDING OPERATIVE CORRIDOR WITH RETRACTOR | 1824 |

| PERFORMING PROCEDURE THROUGH OPERATIVE CORRIDOR | 1826 |

DEVICES, SYSTEMS, AND METHODS FOR INSERTING AND REMOVING SURGICAL WIRES

CROSS REFERENCE TO RELATED APPLICATIONS

This application claims priority to U.S. Provisional Application No. 63/313,841, filed Feb. 25, 2022, which is incorporated herein by reference in its entirety for any and all purposes. This application claims priority to U.S. Provisional Application No. 63/313,809, filed Feb. 25, 2022, which is incorporated herein by reference in its entirety for any and all purposes.

BACKGROUND

There are a wide variety of surgical medical devices. Some of these devices include surgical retractors, surgical retractor systems, surgical retractor stabilization systems, and the like. Of the known surgical medical devices, each has certain advantages and disadvantages. There is an ongoing need to provide alternative surgical medical devices.

SUMMARY

This disclosure provides design, material, manufacturing method, and use alternatives for medical devices. An example retractor blade may include a body having a proximal end and a distal end, and a surgical wire path beginning proximate the proximal end of the body and ending proximate the distal end of the body.

Alternatively or additionally to any of the embodiments in this section, the tractor blade may further include a first opening in communication with the surgical wire path, the first opening is proximate the proximal end of the body, and a second opening in communication with the surgical wire path, the second opening is proximate the distal end of the body.

Alternatively or additionally to any of the embodiments in this section, the surgical wire path may comprise a first surgical wire path and a second surgical wire path.

Alternatively or additionally to any of the embodiments in this section, the first surgical wire path and the second surgical wire path may have a first portion in which the first surgical wire path and the second surgical wire path are parallel and a second portion in which the first surgical wire path and the second surgical wire path converge toward one another.

Alternatively or additionally to any of the embodiments in this section, the first surgical wire path and the second surgical wire path may converge and meet proximate the distal end of the body.

Alternatively or additionally to any of the embodiments in this section, the surgical wire path may have a first section in which the surgical wire path is parallel to a midline of the body, a second section in which the surgical wire path is angled toward the midline of the body, a third section in which the surgical wire path is angled toward the midline of the body, and a fourth section in which the surgical wire path is angled toward the midline of the body.

Alternatively or additionally to any of the embodiments in this section, the surgical wire path may be straight in the first section and the second section and the surgical wire path is curved in the third section.

Alternatively or additionally to any of the embodiments in this section, the surgical wire path has a first portion completely enclosed and a second portion formed from an open channel.

Alternatively or additionally to any of the embodiments in this section, the body may define the surgical wire path.

Alternatively or additionally to any of the embodiments in this section, the retractor blade may further include a tube defining the surgical wire path, wherein the tube may extend along the body from a location proximate the proximal end of the body to a location proximate the distal end of the body.

Alternatively or additionally to any of the embodiments in this section, the tube may be sunk into a face of the body.

Alternatively or additionally to any of the embodiments in this section, the tube comprises a first tube and a second tube spaced distally from the first tube.

Alternatively or additionally to any of the embodiments in this section, the first tube is straight and the second tube is curved.

In another example, a system may comprise a retractor comprising a retractor blade, a surgical wire path extending along the retractor blade, the surgical wire path having a proximal opening and a distal opening, and a surgical wire configured to extend along the surgical wire path from the proximal opening to the distal opening.

Alternatively or additionally to any of the embodiments in this section, the surgical wire path is defined by a tube extending along the retractor blade, the surgical wire path is configured to receive the surgical wire.

Alternatively or additionally to any of the embodiments in this section, the surgical wire path may include a straight section angled toward a midline of the retractor blade, and a curved section angled toward the midline of the retractor blade.

Alternatively or additionally to any of the embodiments in this section, the surgical wire path may be defined by a full enclosure in a first section, and an open channel in a second section.

Alternatively or additionally to any of the embodiments in this section, the surgical wire path may include two surgical wire paths configured to converge at the distal opening.

In another example, a method may comprise placing a retractor blade at a target surgical location, advancing a surgical wire into a proximal opening of the retractor blade and along a surgical wire path of the retractor blade, advancing the surgical wire out of a distal opening of the retractor blade, advancing the surgical wire into a vertebra, and performing a procedure through an operative corridor defined in part by the retractor blade.

Alternatively or additionally to any of the embodiments in this section, the method may further include removing the surgical wire from the vertebral endplate and the retractor blade.

In another example, a retractor blade includes a rear face, a front face, a proximal end, a distal end, wherein the retractor blade defines at least one surgical wire path beginning at a proximal opening in the proximal end and ending in a distal opening at the distal end. The retractor blade can further include a surgical wire extending along the path and out the distal opening. The surgical wire path can define at least two sections. The at least two sections can include a straight section angled toward a midline of the retractor blade; and a curved section angled toward a midline of the retractor blade. The at least one surgical wire path is defined by a channel or trough in the rear face. The at least one surgical wire path can be defined by a tube coupled to the rear face. The retractor blade can define at least two surgical wire paths. The at least two surgical wire paths can converge at a single distal opening. The single distal opening can be disposed along the midline of the retractor blade. The at least two surgical wire paths can be mirrored across a midline of the retractor blade. The at least two surgical wire paths are asymmetric across a midline of the retractor blade. The at least two surgical wire paths are asymmetric across a midline of the retractor blade. There can be more than two surgical wire paths. The at least one surgical wire path can be configured to direct a surgical wire into a vertebral endplate. The retractor blade can be a medial retractor blade of a retractor.

In another example, a method may comprise making a retractor blade and surgical wire available for use, placing the retractor blade at a target surgical location, advancing a surgical wire into a proximal opening of the retractor blade, advancing the surgical wire out of a distal opening of the retractor blade, advancing the surgical wire into a vertebral endplate, and performing a procedure through an operative corridor defined in part by the retractor blade. Performing the procedure can include passing an implant through the operative corridor.

In another example, an apparatus may comprise a surgical shim having a guide, a frame separate from the shim, and a guide tube coupled to the frame and having a tip disposed at an entrance of the guide. The apparatus can further include a retractor blade and the shim. The shim can be coupled to the retractor blade. A surgical wire can extend through the guide tube and the guide. The guide tube can define a plurality of sections, including: a first section; a second section curving away from a desired trajectory; and a third second curving toward the desired trajectory. The desired trajectory can be a trajectory that a surgical wire will assume when leaving the tip. The first section is can be straight. The second section can be distal to the first section. The third section can be distal to the second section. The tip can be at or distal to the third section. The frame can be configured to couple to a shim or a retractor blade. The apparatus can further include an intervertebral implant.

In another example, an apparatus may include a surgical shim having a first guide having a first guide channel configured to receive and direct a surgical wire along a first trajectory, a second guide configured to redirect the surgical from the first trajectory to a second trajectory, and a third guide having a third guide channel configured to receive and direct the surgical wire along the second trajectory. The apparatus can further include a surgical wire extending through the first guide channel along the first trajectory and the third guide channel along the third trajectory. The apparatus can further include a retractor blade. The surgical shim can be coupled to the retractor blade. In an example, the second guide includes a roof.

In an example, a method may include making components available for use, the components including a surgical wire, a retractor blade, an inserter, and a shim; during a spinal procedure, placing the retractor blade in a target surgical location; attaching the shim to the retractor blade; advancing the shim to the target surgical location; attaching the inserter to one or both of the retractor blade and the shim; advancing the surgical wire through a guide tube of the inserter and into and through a guide of the shim; advancing a distal end of the wire out of the guide and into a vertebral endplate; defining an operative corridor with the retractor blade; and passing an implant through the operative corridor.

In an example, an apparatus may comprise a surgical wire remover comprising a first arm having a first pivot, a second arm having a second pivot, a link connecting the first pivot and the second pivot, a plate coupled to the link, a grip surface coupled to the first arm, and a base coupled to the second arm. A surgical wire can extend through the base and between the grip surface and the plate. The apparatus can further include a guard configured to resist removal of a surgical wire from the base.

In an example, a method may comprise, making a surgical wire remover available for se; placing a base of the surgical wire remover at a structure, disposing the surgical wire remover with respect to a surgical wire that is at least partially embedded within bone, and removing the surgical wire from the bone, wherein the removing includes actuating the surgical wire remover. The structure can be a surgical retractor or an articulating arm. Disposing the surgical wire remover with respect to the surgical wire can include: disposing the surgical wire remover such that the surgical wire is disposed between a grip surface and plate of the surgical wire remover. Actuating the surgical wire remover can include: moving arms of the surgical wire remover a first distance; and moving arms of the surgical wire remove a second distance. Removing the surgical wire from the bone can include pressing the base of the surgical wire remover against the structure.

In an example, an apparatus may comprise a surgical wire remover comprising a first arm having a first pivot and a slot, a second arm having a second pivot and a threaded interface, a link connecting the first pivot and the second pivot, a plate coupled to the link, a grip surface coupled to the first arm, a base coupled to the second arm, and an actuator configured to interact with the slot and the threaded interface to decrease a distance between the arms. The apparatus can further include a surgical wire extending through the base and between the grip surface and the plate. The apparatus can further include an implant. The actuator can include a handle and a swivel head bolt.

In an example, an apparatus may comprise a surgical wire remover comprising a first arm having a first pivot, a second arm having a second pivot a link connecting the first pivot and the second pivot, a plate coupled to the link, a grip surface coupled to the first arm, and a base coupled to the second arm, wherein the surgical wire remover comprises an offset cam interface.

Alternatively or additionally to any of the embodiments in this section, the apparatus can further include a surgical wire extending through the base and between the grip surface and the plate. The apparatus can further include an intervertebral implant.

In an example, an apparatus may comprise a surgical wire remover comprising a first arm having a first pivo, a second arm having a second pivot, a link connecting the first pivot and the second pivot, a plate coupled to the link, a grip surface coupled to the first arm, and a base coupled to the second arm, wherein the surgical wire remover further comprises a spring mechanism that urges the first and second arms apart. The spring mechanism can include: a pair of spring members, each connected to a respective arm and the other spring member; a leaf spring mechanism; or a torsion spring mechanism. The apparatus can further include a surgical wire extending through the base and between the grip surface and the plate. The apparatus can further include a guard configured to resist removal of a surgical wire from the base.

In an example, an apparatus may comprise a surgical wire remover comprising a first surgical wire grip and a second surgical wire grip, wherein each of the grips is configured to grip the surgical wire when canted relative to the surgical wire and release the surgical wire when perpendicular to the surgical wire, and a trigger configured such that actuation of the trigger causes gripping, movement, and then release of the surgical wire. The apparatus can further include a surgical wire extending through the base and between the grip surface and the plate. The apparatus can further include a In an example, an apparatus may include a surgical wire remover configured to laterally receive a surgical wire into a base via a path, wherein the path includes one or more features configured to increase a difficulty in inserting and removing the surgical wire laterally through the path. The one or more features can include: at least one projection into the path or at least one bend in the path. The apparatus can further include a sterilized surgical wire extending through the base.

In an example, an apparatus may comprise a surgical wire remover configured to laterally receive a surgical wire into a base via a path; and a guard resisting entry of a surgical wire laterally through the path. The guard can include a flexible arm. The guard can include a spring clip. The spring clip can be biased closed by a torsion spring.

In an example, a retractor body may have a retractor arm, a retractor blade coupled to the retractor arm, and a surgical wire remover coupled to the retractor arm.

Alternatively or additionally to any of the embodiments in this section, the surgical wire remover can be configured to be attached and detached from the retractor arm.

Alternatively or additionally to any of the embodiments in this section, the surgical wire remover can include an extension, wherein the extension mates with a feature of the retractor arm. The extension can be a pin. The feature can be a hole, divot, or groove. The feature can be a slot or groove of the retractor blade. The surgical wire remover can be coupled to the retractor arm via the retractor blade. In an example, the feature is a slot configured to receive a portion of a supplemental retractor. The feature can be an articulating arm connector. The surgical wire remover can have a single user grip feature. At least a portion of the retractor arm can act as a second user grip feature that cooperates with the single user grip feature of the surgical wire remover to permit actuation by a user.

In an example, an apparatus may include a surgical wire remover comprising a grip configured to directly interact with a grippable feature of a surgical wire; and a base configured to abut a component of a retractor.

In an example, an apparatus may comprise a surgical wire remover comprising a gear having teeth configured to directly interact with a surgical wire; and a handle configured to rotate the gear.

BRIEF DESCRIPTION OF THE DRAWINGS

FIG. 10 is schematic diagram of an illustrative method.

FIG. 18 is a schematic diagram of an illustrative method of using a wire during a spinal procedure.

DETAILED DESCRIPTION

Figures 1A, 1B:
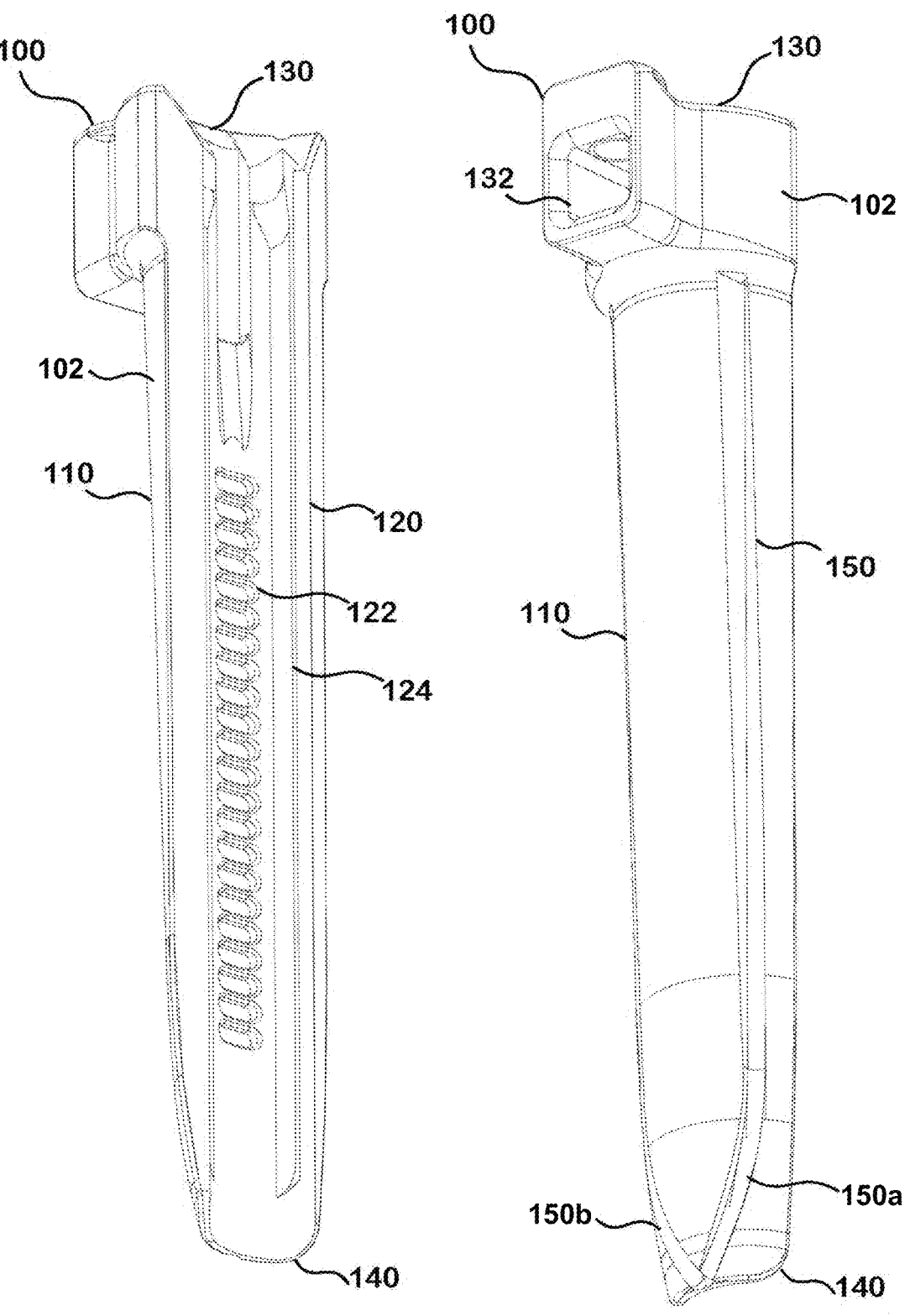
FIG. 1A is a schematic first perspective view of an illustrative retractor blade.
FIG. 1B is a schematic second perspective view of the illustrative retractor blade depicted in FIG. 1A.
Figure 2:
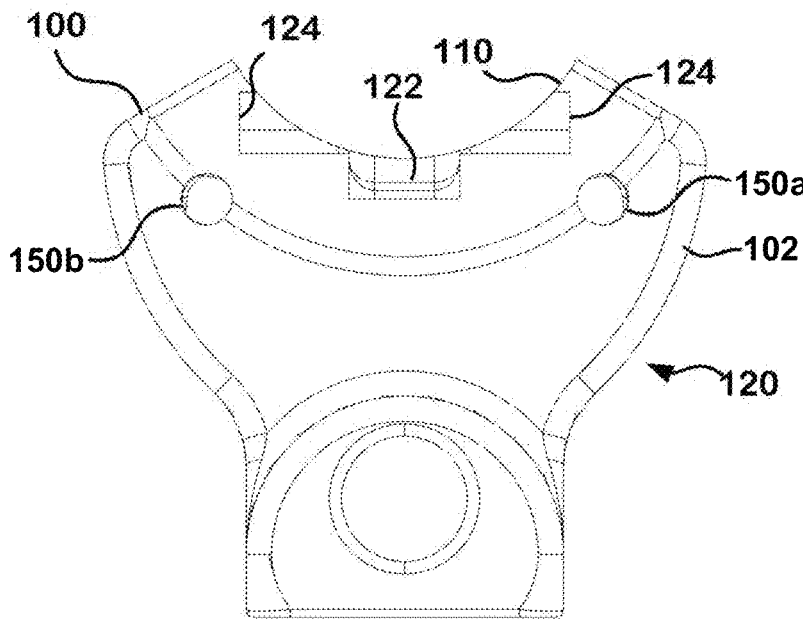
FIG. 2 is a schematic top view of the illustrative retractor blade depicted in FIG. 1A.
Figure 3:
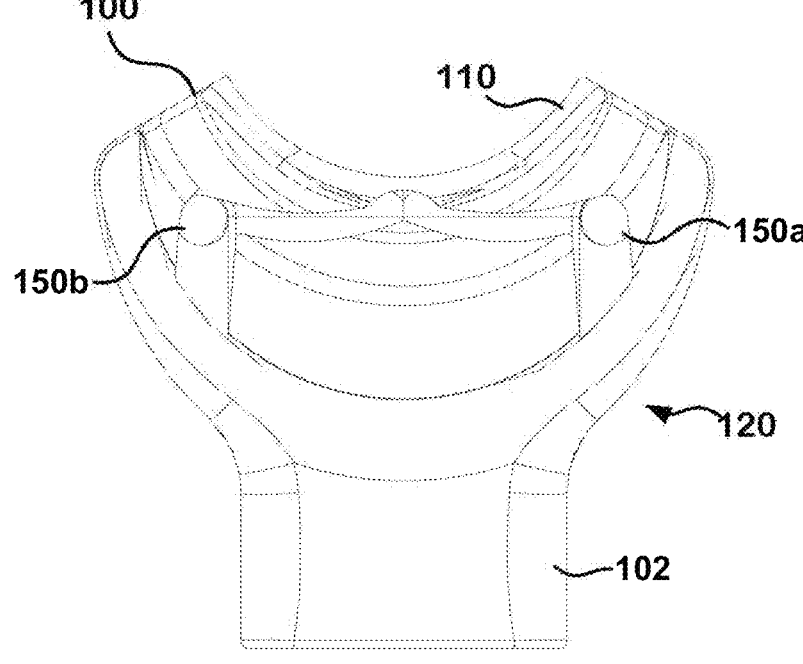
FIG. 3 is a schematic bottom view of the illustrative retractor blade depicted in FIG. 1A.

A trend in the medical community is the move away from performing surgery via traditional "open" techniques in favor of minimally invasive or minimal access techniques. Open surgical techniques are generally undesirable in that they typically require large incisions and high amounts of tissue displacement to gain access to the surgical target site, which produces concomitantly higher amounts of pain, lengthened hospitalization, and higher morbidity in the patient population. Less-invasive surgical techniques (including so-called "minimal access" and "minimally invasive" techniques) are gaining favor due to the fact that they involve accessing the surgical target site via incisions of substantially smaller size with greatly reduced tissue displacement requirements. This, in turn, reduces the pain, morbidity, and cost associated with such procedures.

Less-invasive surgical access systems often include retractors used to form and expand a surgical corridor. Shims can be used to enhance capabilities of retractors, such as the retractors described in U.S. Pat. No. 7,905,840 (filed Oct. 18, 2004); U.S. Pat. No. 8,137,284 (filed Oct. 8, 2003); and US 2021/0007727 (filed Jun. 18, 2020), which are all hereby incorporated herein by reference for any and all purposes. Example shims include those described in U.S. Pat. No. 7,905,840 (filed Oct. 18, 2004) and U.S. application Ser. No. 17/390,448 (filed Jul. 30, 2021), both of which are hereby incorporated herein by reference in their entirety for any and all purposes.

Less-invasive surgical access systems can also include surgical wires. Surgical wires are used in medical procedures, such as in orthopedic procedures. Such wires can be used to reduce or stabilize structures or as guide wires for subsequent instruments or implants. Surgical wires can take any of a variety of forms and are known by a variety of names or descriptions, such as Kirschner wires (K-wires), Steinmann pins, pins, or fine rods. While surgical wires are sometimes threaded, they often have smooth exteriors. Surgical wires often have sharp tips to facilitate insertion to bone. While such wires tend to be stiff enough for insertion into bone, they often have some degree of flexibility. While surgical wires are useful, they can be difficult to insert or remove, especially if the wires are bent.

Disclosed devices, systems, and methods include devices, systems, and methods for inserting and removing surgical wires. For example, a surgical wire can be part of a system that includes retractor blade, a surgical shim coupled to a retractor blade, or both, where the retractor blade, the surgical shim, or both may define one or more paths for receiving the surgical wire to follow.

The paths can be, for example, one or more openings, cannulations, paths, tubes, tunnels, extensions, other structures, or combinations thereof. The surgical wire can be routed through the front, back, middle, inside, and/or outside of the retractor blade. Alternatively or additionally, the wire can be routed through the shim and into a vertebral body. The paths can be configured to ultimately guide a wire along a trajectory for insertion into bone, such as a vertebral endplate. The paths can facilitate the changing or maintaining of a trajectory of the wire (e.g., relative to a length of the retractor blade, relative to the patient's skin, or relative to an operative corridor). For example, the paths can modify the trajectory of the surgical wire by modifying an angle of a trajectory of the wire from an initial insertion angle to an angle along which the wire will be inserted into patient tissue. The changing of the angle can be beneficial because surgical corridors used in minimally invasive surgery can be relatively constrained, which can limit the ability of a user to both insert the wire down the corridor and angle the wire into a desired anatomical structure. The paths can be so configured via a fixed or expandable pathway to accommodate the trajectory of the surgical wire. Further, the paths can be configured to protect both the wire and patient tissue during insertion, whether insertion is achieved with or without power. The retractor blade can include one or more features to guide fixation instruments and the one or more features can vary in shape and size for achieving desired trajectory and ease of insertion.

In some examples, some or all of the path can be defined by a tube or tunnel through retractor blade material (e.g., the path can be a tunnel completely surrounded by retractor blade material). In some examples, the path is gently or severely curved. In one example, the path may be gently or severely curved by having one or more S-shaped curves. The curves can cross the longitudinal midline of the retractor blade one or more times. In some examples, the distal exit of the path on the blade is aligned with an extension piece beyond or coupled to the blade. For instance, there may be a shim or blade extender having a portion distal to the retractor blade. The path can be such that the surgical wire exits the distal opening of the blade and enters the extension piece. The extension piece can facilitate easier surgical wire insertion and can help direct the k-wire into a vertebral endplate or other anatomy at a desired trajectory. In some examples, the path has a distance longer than a length of the retractor blade.

In some examples, the path can leave and optionally return to the retractor blade. For example, there can be one or more rigid or flexible tubes or other structures coupled to the retractor into or through which the path can continue. The structures can be sufficiently flexible to deform out of the way when the retractor blade is inserted into the patient. The tube can be coupled to the retractor blade or spaced away from the retractor blade.

The surgical wire can exit the path through the retractor blade at a distal end of the retractor blade at a predetermined angle (e.g., approximately 35 degrees or other suitable degree relative to a longitudinal axis of the retractor blade). The predetermined angle or trajectory can be configured to cause the surgical wire to enter the superior or inferior vertebral endplates of a patient where the retractor blade is a medial retractor blade of a retractor.

The retractor blade may have one or more paths. For example, the blade may have multiple paths having different trajectories selectable by a user (e.g., the blade may have a path for a 25-degree trajectory, another for a 30-degree trajectory, and yet another for a 35-degree trajectory). In some examples, the different paths may have selectable cranial or caudal trajectories (e.g., for guiding the surgical wire into either inferior or superior endplates). In some examples, the retractor blade can include paths that are symmetric (e.g., mirrored) across the longitudinal midline of the retractor blade. In yet further examples, the paths can be asymmetric across the longitudinal midline.

One or more of these features can be implemented to provide benefits relating to the use of surgical wires during surgery. One particular use case can be to secure the retractor blade with the surgical wire during surgery (e.g., a prone lateral interbody fusion surgery). The securing of the retractor blade with the surgical wire can facilitate maintaining an operative corridor through which an implant can be placed within the patient's intervertebral space.

FIGS. 1A-7 illustrate an illustrative retractor blade 100 having a body 102 with a rear face 110, a front face 120, a proximal end 130, and a distal end 140. The body 102 of the retractor blade 100 further defines one or more paths 150 (e.g., one path, two paths which can be referred to as a first path 150*a* and a second path 150*b*, as depicted in FIG. 1B, etc.) through or otherwise along the body 102 of the retractor blade 100 for guiding the surgical wire.

The body 102 may be formed from one or more components. In one example, the body 102 may be a single component monolithically formed. Alternatively, the body 102 may be formed from two or more components coupled together in an suitable manner.

The rear face 110 is configured to interact with (e.g., contact) with patient tissue during use. For example, the rear face 110 can have a smooth curve. The rear face 110 can be so configured by being disposed in a position to contact patient tissue based on how the blade 100 is configured to couple to a retractor body.

The front face 120 is configured to face the surgical corridor during use. The rear face 110 can be so configured by being disposed in a position to face the surgical corridor based on how the blade 100 is configured to couple to a retractor body.

The front face 120 includes a plurality of ratchet-like latitudinal grooves 122, which can be used for coupling or retaining one or more features or components with respect to the retractor blade 100, such as one or more blade extenders or surgical shims. In addition, there may be one or more additional longitudinal grooves 124 for retaining one or more features, such as the one or more blade extenders or surgical shims. The grooves 124 can be used to retain, for example, one or more light cables.

The proximal end 130 can include one or more couplings 132 configured for coupling the retractor blade 100 to a retractor body or a retractor arm thereof. The couplings 132 can be any of a variety of styles to suitably connect the retractor blade 100.

Figure 4:
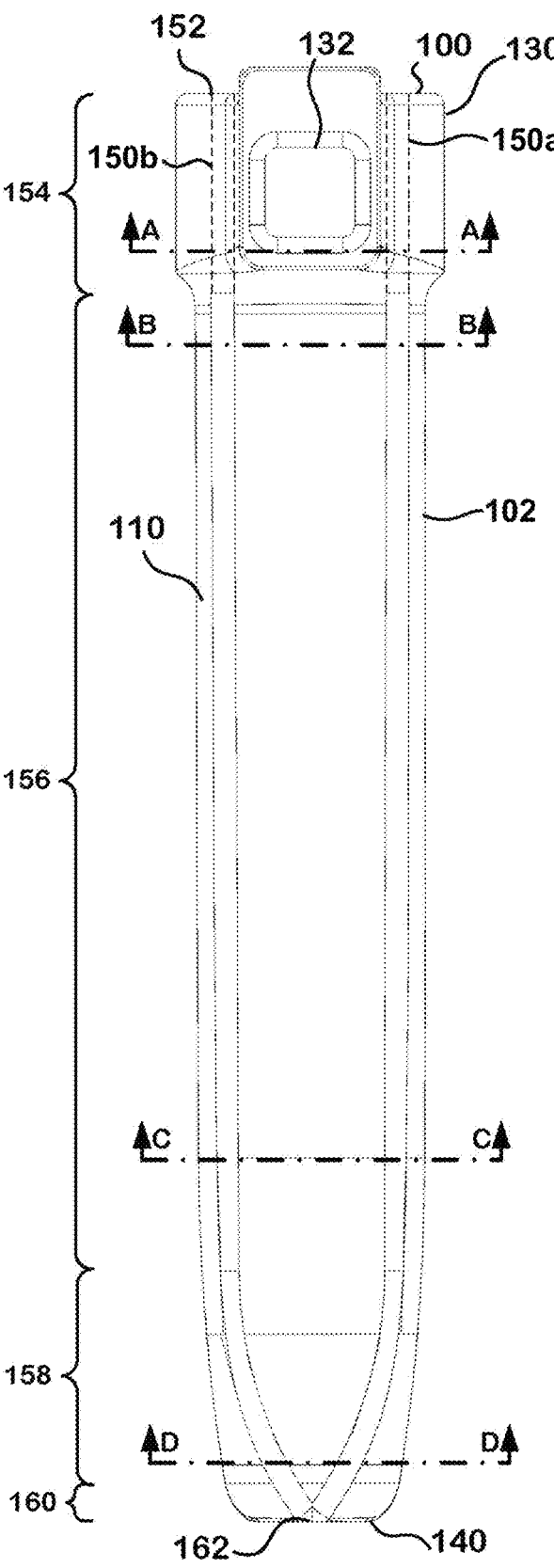
FIG. 4 is a schematic rear view of the illustrative retractor blade depicted in FIG. 1A.
Figures 5A, 5B, 5C, 5D:
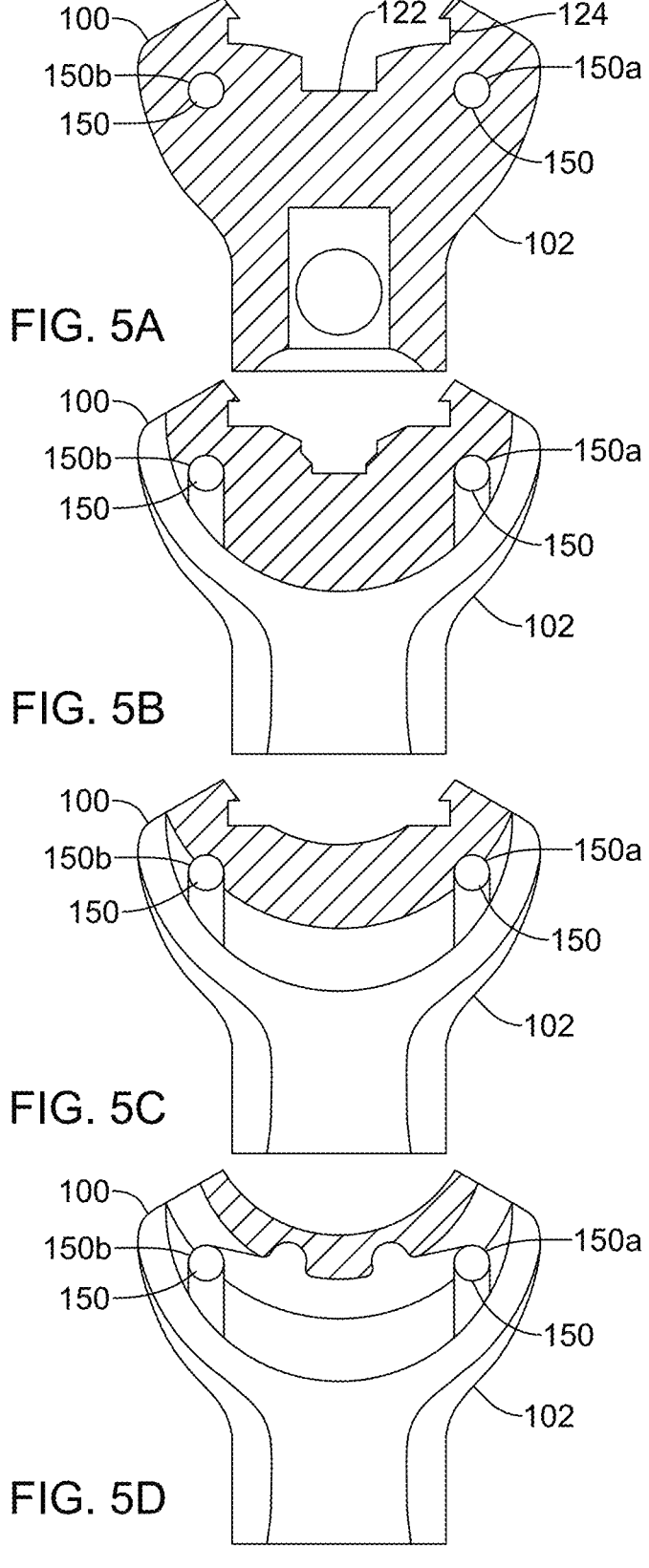
FIG. 5A is a schematic cross section view of the illustrative retractor blade depicted in FIG. 1A, taken along line A-A of FIG. 4.
FIG. 5B is a schematic cross section view of the illustrative retractor blade depicted in FIG. 1A, taken along line B-B of FIG. 4.
FIG. 5C is a schematic cross section view of the illustrative retractor blade depicted in FIG. 1A, taken along line C-C of FIG. 4.
FIG. 5D is a schematic cross section view of the illustrative retractor blade depicted in FIG. 1A, taken along line D-D of FIG. 4.
Figure 6:
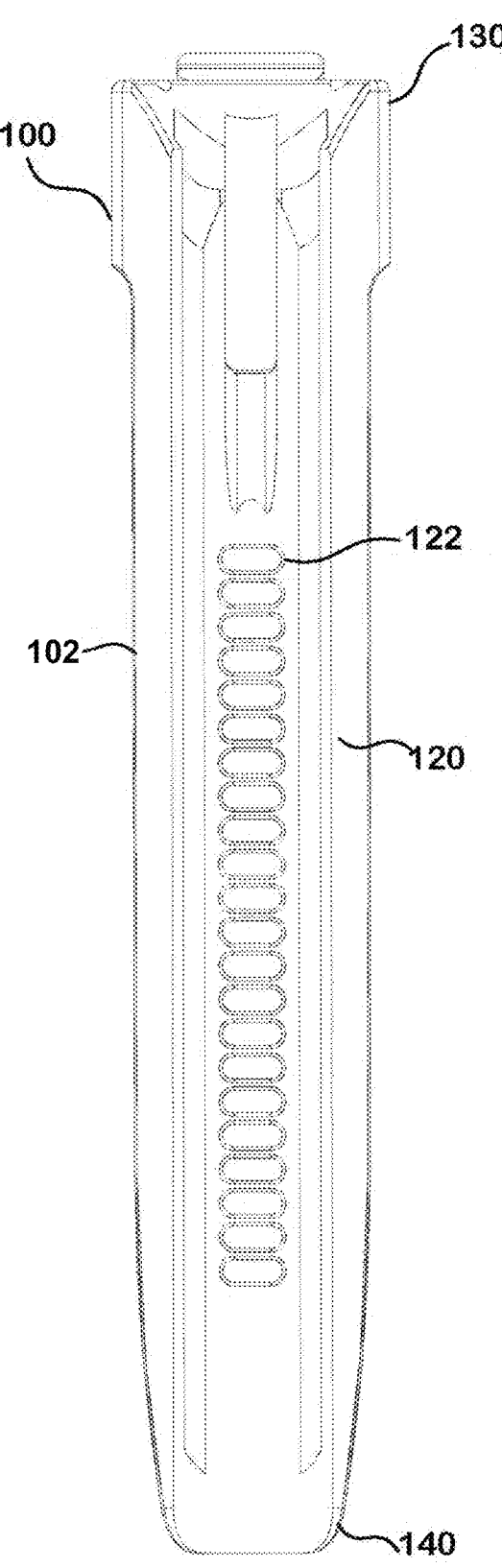
FIG. 6 is a schematic front view of the illustrative retractor blade depicted in FIG. 1A.
Figure 7:
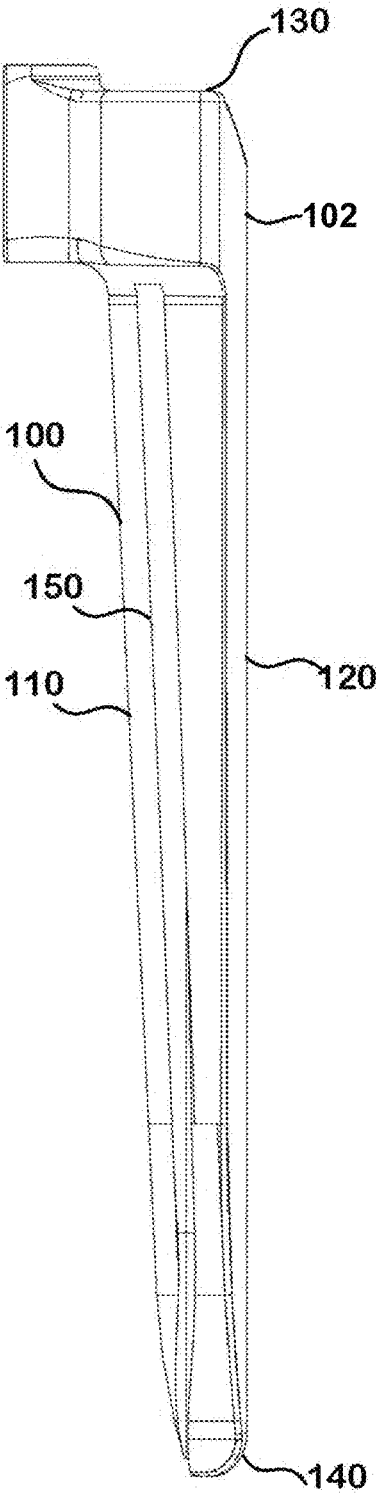
FIG. 7 is a schematic side view of the illustrative retractor blade depicted in FIG. 1A.

The paths 150 can be configured for guiding a surgical wire. The paths 150 can be one or more openings, cannulations, paths, tubes, other structures, or combinations thereof. The paths 150 can be sized and shaped to receive and usably guide a surgical wire. The paths 150 can begin at a proximal opening 152 and end at a distal opening 162 and be considered as having multiple sections (e.g., a first section 154, a second section 156, a third section 158, and a fourth section 160, as depicted in FIG. 4. The paths 150*a*, 150*b* may be symmetrical or asymmetrical about a midline of the body 102 of the retractor blade 100, as desired, along one or more of the multiple sections 154, 156, 158, 160. A cross-section of the first section 154 is depicted in FIG. 5A, cross-sections of the second section 156 are depicted in FIGS. 5B and 5C, and a cross-section of the third section 158 is depicted in FIG. 5D.

The proximal opening 152 can be disposed at or otherwise proximate the proximal end 130 of the body 102 of the blade 100. The proximal opening 152 can be configured to receive the surgical wire. For example, the proximal opening 152 can be chamfered or otherwise configured to facilitate easy insertion of the surgical wire.

The distal opening 162 can be disposed at or otherwise proximate the distal end 140 of the body 102 of the blade 100. The distal opening 162 can be configured to receive the surgical wire and allow the surgical wire to exit the paths 150 for coupling with a vertebra.

The first section 154 can be a portion where the paths 150 pass through a proximal section of body 102 of the retractor blade 100. In the first section 154, the paths 150 can be completely enclosed (e.g., by material of the body 102, etc.)

Additionally or alternatively the paths 150 can be substantially parallel to the length or a midline of the body 102 retractor blade 100 or the first path 150*a* and the second path 150*b* may be parallel to one another, the midline, or both. In the illustrated second section 156, third section 158, and fourth section 160, the paths 150 are open channels or troughs in the rear face 110 of the retractor blade 100. While in the second section 156, the paths 150 are substantially straight and slightly angled toward the longitudinal midline of the body 102 of the retractor blade 100. The longitudinal midline of the body 102 of the retractor blade 100 can be a midline extending along and parallel to the length of the retractor blade 100, such as when viewed from the front or rear of the retractor blade 100. While in the third section 158, the paths 150 are curved and more aggressively angle toward the midline of the body 102. While in the fourth section 160, the paths 150 converge toward one another and meet at the distal openings 162 proximate the distal end 140 of the body 102. These sections and configurations of the path 150 guide and urge the surgical wire.

The proximal openings 152 and the exit openings 162 of the paths 150 are not shifted with respect to each other on a front-rear axis of the blade 100 and instead are only shifted along a length of the body 102 of the retractor blade 100 (e.g., the exit opening 162 is distal to the proximal opening 152) and along the latitude of the body 102 of the retractor blade 100 (e.g. the exit opening 162 is medial to the proximal openings 152). Further, the first path 150A and the second path 150B are mirrored with respect to each other across the midline of the body 102.

In other examples, the paths 150 can take other shapes, including shifting within the front-back axis. Further, the paths 150 need not be mirrored with respect to each other; they may be asymmetric across the midline. In some examples, the different paths 150 can cause the surgical wire to exit at different trajectories, such that a surgeon can select a desired trajectory. Further, there may be more than two paths 150. For example, there may be any number of paths 150, each of which can have different characteristics with respect to each other. Further, while in many sections 156, 158, 160, the paths 150 take the form of open J-shaped channels or troughs, in some implementations, the paths 150 can have roofs, narrowed necks, or other features that resist the surgical wires from leaving the paths 150 before they reach the exit opening 162. In the illustrated example, because the paths 150 are in the form of channels or troughs in the material of the retractor blade 100, the paths do not rearwardly extend beyond the rear face 110 of the body 102 of the retractor blade 100. Such a feature can be beneficial in maintaining a relatively smooth curve of the tissue-contact surface of the retractor blade 100.

Figure 8:
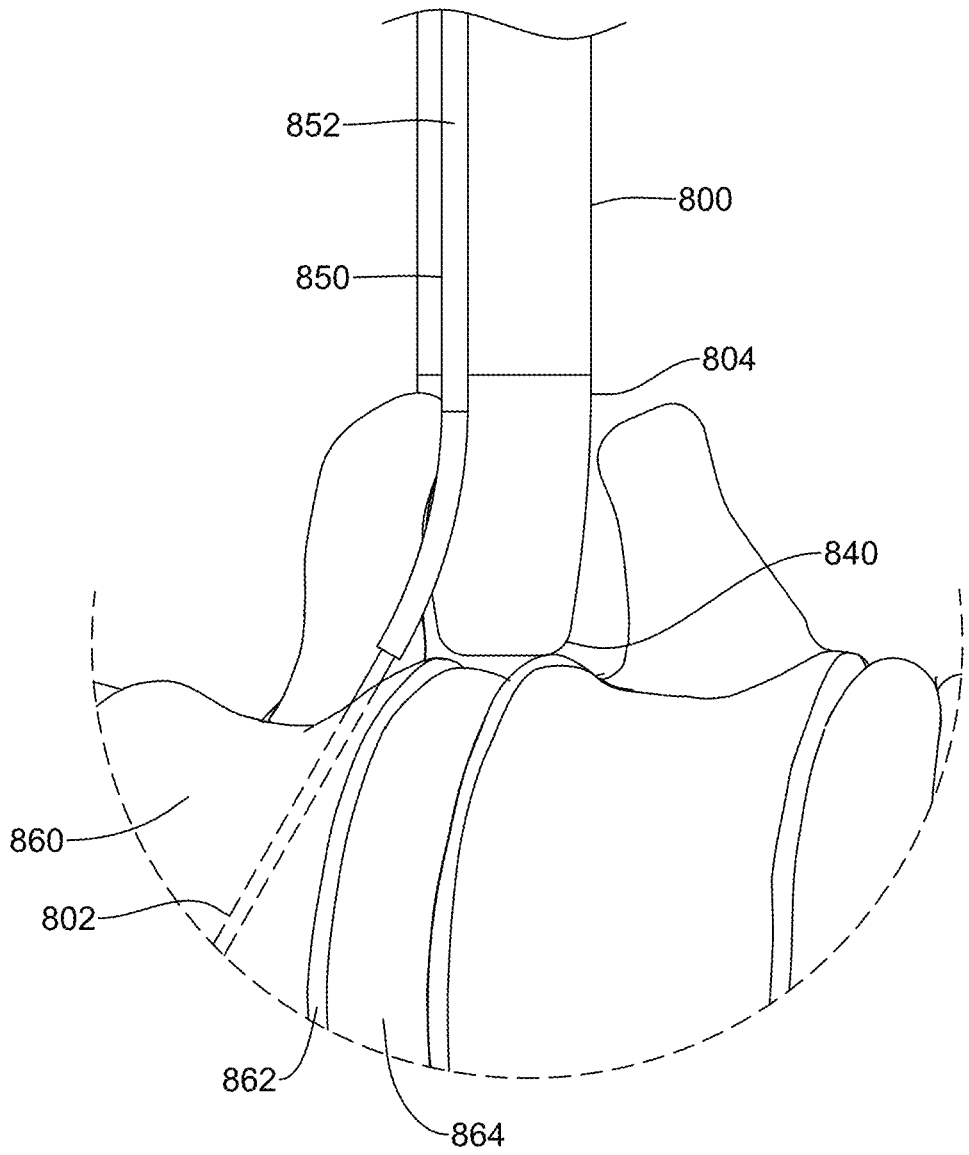
FIG. 8 is a schematic rear view of an illustrative retractor blade, with a surgical wire inserted therethrough and into a vertebral body.
Figure 9:
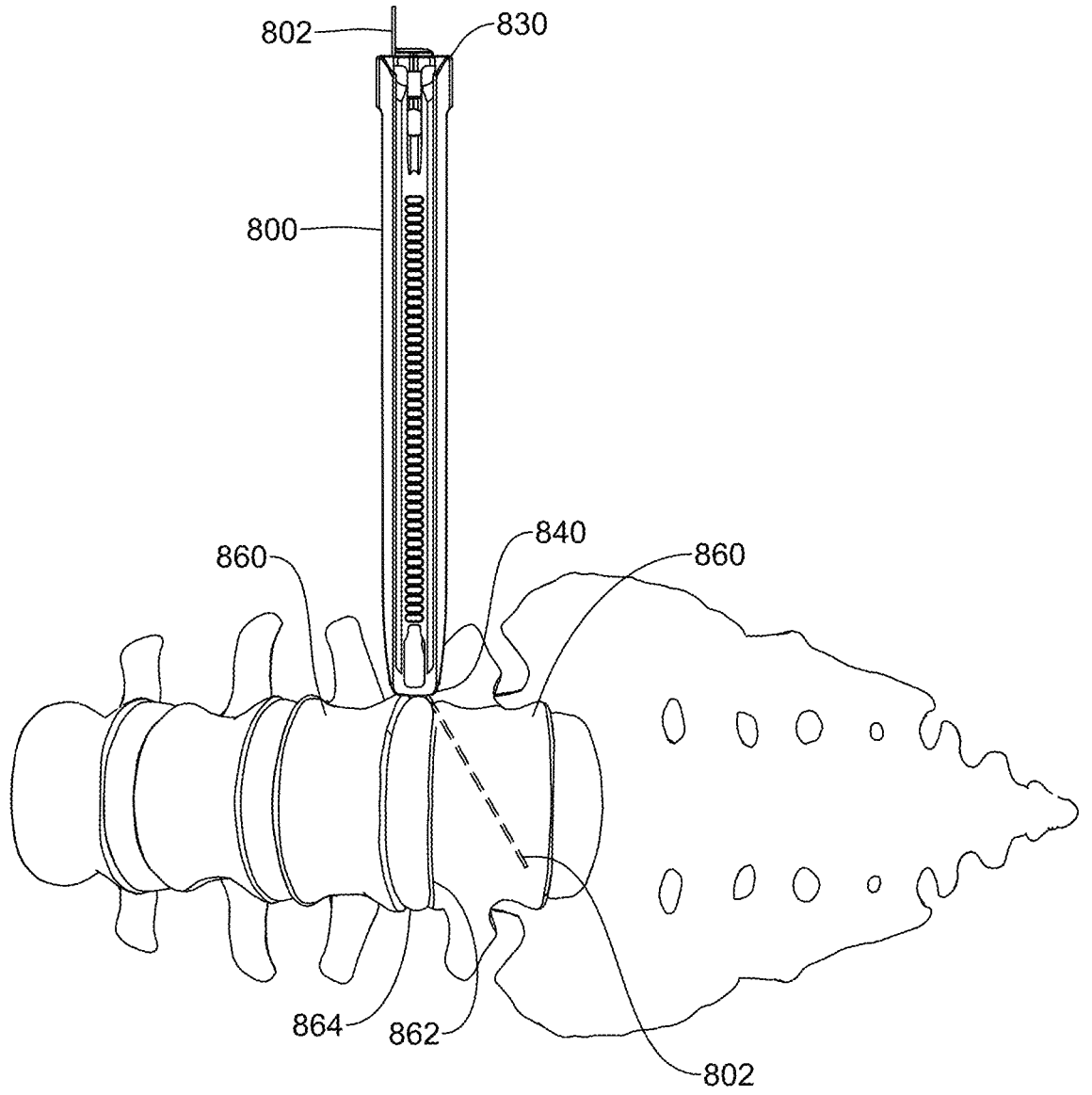
FIG. 9 is a schematic front view of the illustrative retractor blade depicted in FIG. 8, with the surgical wire inserted therethrough and into a vertebral body.

FIGS. 8 and 9 illustrate an illustrative retractor blade 800 having a body 804 with a proximal end 830 and a distal end 840 with a surgical wire 802 extending therethrough and into a vertebral body 860 having a vertebral end plate 862 proximate an intervertebral disc 864. The surgical wire 802 can be routed through the front, back, and/or middle of the retractor blade 800 and into the vertebral body 860.

The blade 800 has one or more features in common with blade 100. In one example configuration, the blade 800 may have a path 850 extending along the body 804 and defined by a tube 852 coupled to the rear face of the body 804. The tube 852 may extend along the body 804 of the retractor blade 800 from a position proximate the proximal end 830 to a position proximate the distal end 840. In some examples, the tube 852 is partially sunk into the rear face of the body 804, but this is not required.

The tube 840 may be formed from one or more components. In one example, the tube 840 may be formed from a single tubular component. In another example, the tube 840 may be formed from two or more tubular components coupled together, contacting one another, spaced from one another, or a combination thereof.

FIG. 10 illustrates an example method 1000 of using a retractor blade as described herein or one or more other suitable retractor blades during a spinal procedure. In an example, the procedure is a lateral interbody fusion procedure performed while the patient is in a prone position, but the techniques herein can be applicable to other procedures, including, lateral interbody fusions, transforaminal interbody fusions, anterior lumbar interbody fusions, posterior interbody fusions, procedures at the cervical spine, procedures at the thoracic spine, procedures at the lumbar spine, procedures while the patient is in the prone position, procedures while the patient is in the supine position, procedures while the patient is in a lateral decubitus position, other procedures, or combinations thereof. The method can begin with operation 1002.

Operation 1002 includes making components available for use. The component can include any of the components described elsewhere herein, such as a retractor (e.g., having retractor blade 100) and surgical wire, among others, variations thereof, and combinations thereof. In some examples, making available for use includes providing the parts of the components. The operation 1002 can include removing such components from sterile packaging and arranging them from use in an operating room.

Operation 1010 includes, during the spinal procedure, placing a retractor in a target surgical location. The surgical location can be, for example, an intervertebral disc space at a spinal level where a procedure is to be performed. In an example, the operation 1010 can include advancing one or more blades of the retractor (e.g., blade 100 or other suitable blade of a retractor) over a dilation system such that a center retractor blade is the posterior most blade of the retractor. Following operation 1010, the flow of the method 1000 can move to operation 1012.

Operation 1012 includes advancing a surgical wire into a proximal opening of the retractor blade (e.g., proximal opening 152 of blade 100). In some examples, the surgical wire can be advanced under power. Following operation 1012, the flow of the method 1000 can move to operation 1014.

Operation 1014 includes advancing the wire through the path. The advancing the wire through the path (e.g., the path 150) can include causing or permitting the material defining the path to bend the wire such that the distal end of the wire follows a trajectory defined by the path. In some examples, this advancing can include advancing the surgical wire through one or more sections of the path, each of which may differently control a path or trajectory of the surgical wire. In other examples, the path does not substantially change the direction of the wire but instead maintains a general trajectory of the wire. Following operation 1014, the flow of the method 1000 can move to operation 1016.

Operation 1016 can include advancing a distal end of the surgical wire out of a distal opening of the blade (e.g., distal opening 162 of blade 100). In many examples, the surgical wire exits the distal opening and directly enters the disc. In other examples, the wire does not directly enter the disc. Following operation 1016, the flow of the method 1000 can move to operation 1018.

Operation 1018 can include advancing the distal end of the wire into a vertebral endplate. Sufficient amounts of the wire can be advanced into the vertebral body to facilitate securing the retractor blade. In this manner, the wire resists movement of the blade, such as posteriorly towards nerve tissue located in the posterior portion of the psoas muscle. Following operation 1018, the flow of the method 1000 can move to operation 1020.

Operation 1020 can include expanding the operative corridor with the retractor. For example, the retractor blades are separated, providing an operative corridor through which instruments or implants can be advanced to the target site. Following operation 1020, the flow of the method 1000 can move to operation 1022.

Operation 1022 can include performing one or more procedures through the operative corridor. Any number of procedures may be performed on the spine through the lateral access corridor, such as a fusion procedure, a total disc replacement, or a corpectomy, among other procedures. The procedure can include implanting an implant through the operative corridor.

Example implants that can be included with or used with systems or methods described herein can include intervertebral implants. Example intervertebral implants can be fixed or expandable. Example implants include: those described in U.S. Pat. Nos. 7,815,682; 7,918,891; 8,187,334; 8,246,686; 8,287,597; 8,361,156; 8,574,301; 8,608,804; 8,673,005; 8,685,105; 8,814,940; 8,920,500; 9,180,021; 9,186,261; 9,192,482; D594,986; D599,019; D621,509; D671,645; D674,092; D675,320; D696,402; D708,747; D735,336; D747,485; D750,252; D754,346; D759,248; D767,762; D770,405; 9,474,627; 9,486,329; D781,423; 9,744,053; D788,307; D788,308; D791,949; D797,934; 9,445,918; and 10,675,158, which are herein incorporated herein by reference in their entirety for any and all purposes.

Figure 11:
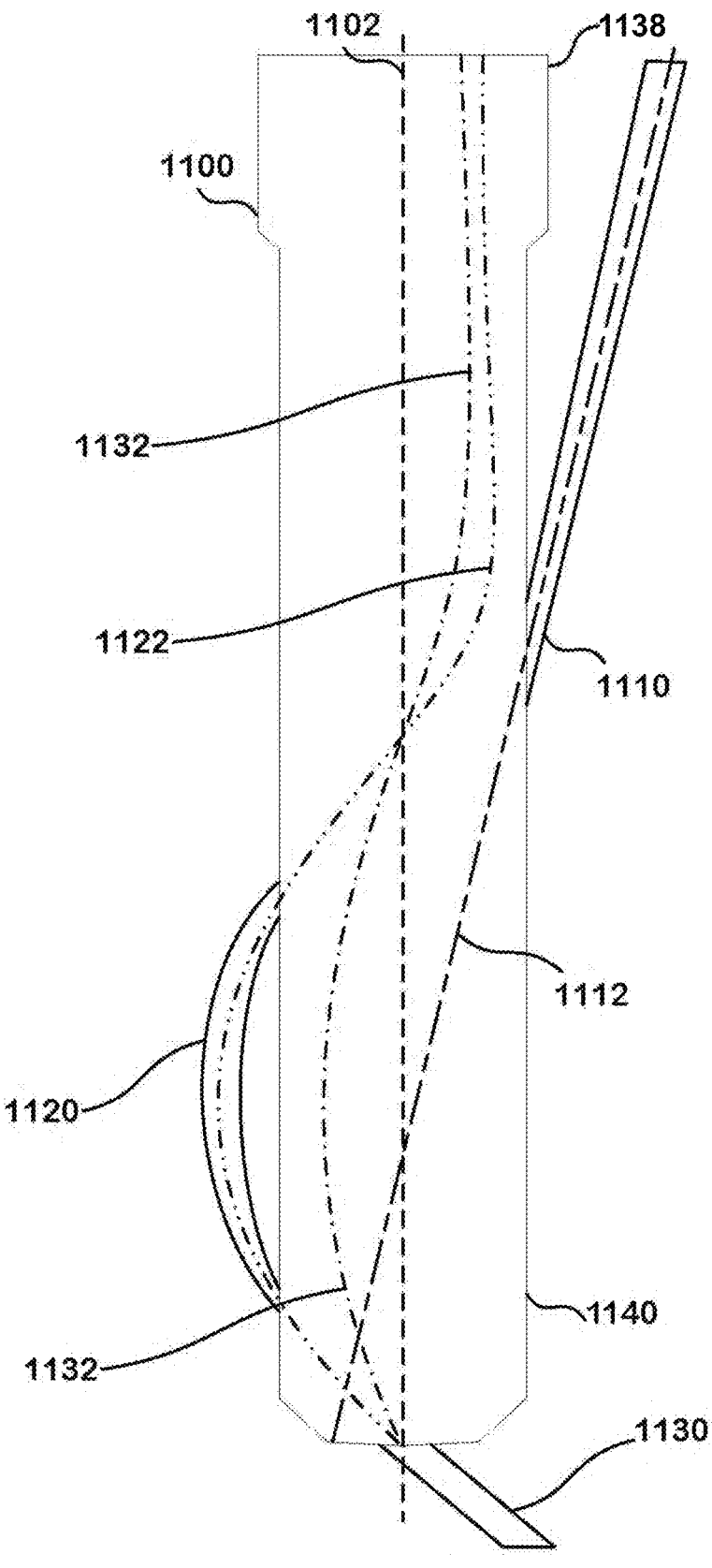
FIG. 11 is a schematic view of illustrative paths relative to a retractor blade.

FIG. 11 illustrates a front view of a further example retractor blade 1100 having a proximal end 1138, a distal end 1140, and multiple different paths. The longitudinal midline 1102 of the retractor blade 1100 is also illustrated. While first, second, and third paths 1112, 1122, 1132 and first, second, and third extensions 1110, 1120, 1130 are simultaneously illustrated, they need not all be present in a single retractor blade 1100. The paths 1112, 1122, 1132 can include one or more features of the paths described elsewhere herein and can have additional features described below. The extensions 1110, 1120, 1130 can be tubes, ducts, or other features that extend beyond (e.g., stick out from) the general blade shape of the retractor blade and help direct the surgical wires on the path. In some instances, the entrance of the extension is beyond the retractor blade 1100 and is designed to be the first location into which the surgical wire is to be inserted (see, e.g., first extension 1110). In some instances, the entrance of the extension is coupled to the retractor blade 1100 and is designed to receive the surgical wire directly or indirectly from a path through, at, or near the retractor blade (see, e.g., second extension 1120 and third extension 1130). In some instances, the exit of the extension is coupled to the retractor blade 1100 and is designed to direct the surgical wire into a path through or at the retractor blade 1100 (see, e.g., first extension 1110 and second extension 1120). In some instances, the exit of the extension is separate from the retractor blade 1100 (see, e.g., third extension 1130). In some examples, the extensions 1110, 1120, 1130 can be sized and shaped relative to the path in the blade 1100 such that the extensions can slide in and out of the path. In some examples, single extension can run the entire length of the path and slide in and out of the blade. For instance, the extension can be contained within the blade to ease insertion of the blade, deployed from the blade (e.g., by pushing the extension distally), and then the surgical wire can be inserted therethrough.

The first path 1112 illustrates an example path that is straight from its entrance point on the retractor blade 1100 to the exit at the midline 1102 of the retractor blade 1100 at the distal end 1140 of the retractor blade 1100. Further, the first path 1112 begins at a location spaced away from the retractor blade 1100 and intersects the retractor blade 1100 approximately midway down the retractor blade 1100. A first extension 1110 may, but need not, be provided to facilitate insertion of a surgical wire into the portion of the first path 1112 that passes along or through the retractor blade 1100. The first extension 1110 can be a tube or other feature that has an entrance separate from the retractor blade 1100 and has an exit coupled to the retractor blade 1100. The first extension 1110 can be configured to guide the surgical wire to the retractor blade 1100 such that the retractor blade 1100 can continue to guide the surgical wire.

The second path 1122 illustrates an example S-shaped path. The second path 1122 begins at the proximal end of the retractor blade 1100 and ends at the distal end of the retractor blade 1100. At one point, the second path 1122 leaves the retractor blade 1100 and continues into a second extension 1120. The second extension 1120 continues the general shape of the curve of the second path 1122 away from the retractor blade 1100 before returning to the retractor blade 1100. This permits the path 1122 to have a curve with a width greater than a width of the retractor blade 1100, which can facilitate curving or otherwise manipulating the surgical wire. The second path 1122 can end proximate the midline 1102 of the retractor blade 1100 at the distal end 1140 of the retractor blade 1100. Optionally, the second path 1122 can continue into the third extension 1130.

The third path 1132 illustrates an example S-shaped path. The third path 1132 begins at the proximal end of the retractor blade 1100 and ends at the distal end of the retractor blade 1100. Though, optionally, as illustrated, the third path 1132 can continue into the third extension 1130. The third path 1132 begins on one side of the midline 1102 of the retractor blade 1100 and then curves over to the other side of the midline before finally terminating proximate to the midline 1102 of the retractor blade 1100 at the distal end of the retractor blade 1100.

Figure 12:
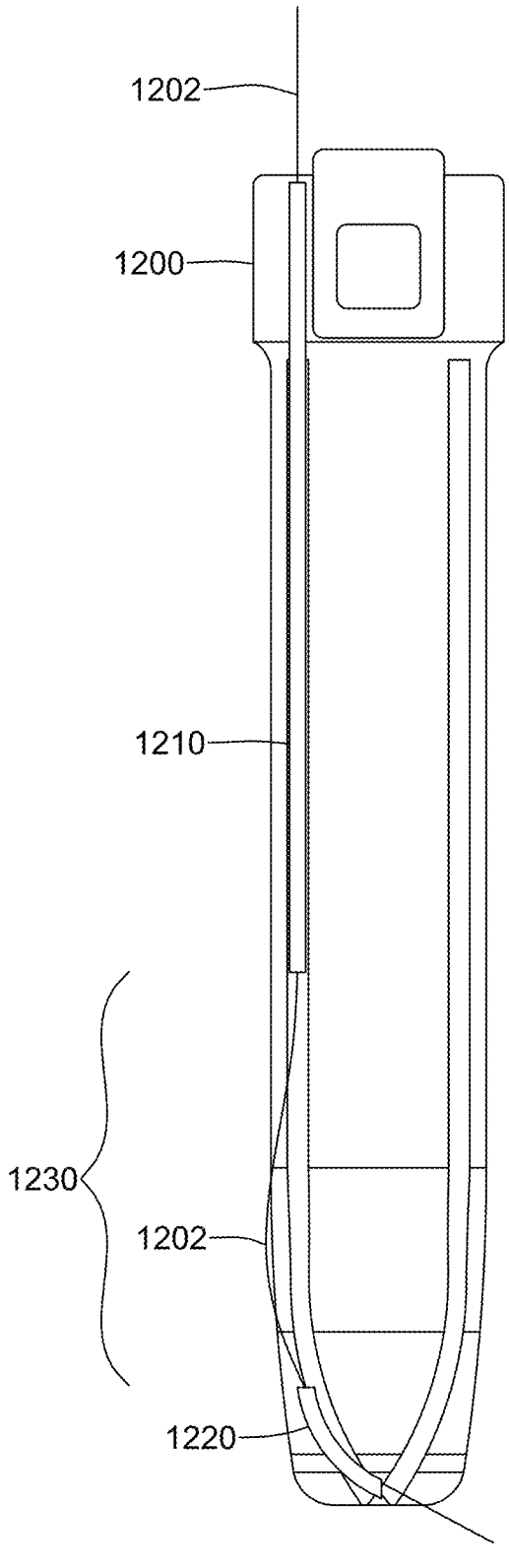
FIG. 12 is a schematic view of an illustrative retractor blade with a wire extending therethrough.

FIG. 12 depicts an illustrative retractor blade 1200. In the example of FIG. 12, a wire 1202 is following a path defined by a first tube 1210 and a second tube 1220. In the illustrated example, the first tube 1210 is straight (e.g., straight in a longitudinal direction) and directs the wire 1202 toward a proximal opening of the second tube 1220. The second tube 1220 is curved (e.g., curved in a longitudinal direction) and configured to redirect the wire 1202 from a first trajectory to a second trajectory. The second trajectory can be oblique to a length of the retractor blade 1200. A distal opening of the first tube 1210 is separated from the proximal opening of the second tube 1220 by a gap 1230. As illustrated, the gap 1230 can provide a space for the wire 1202 to bend or flex to a greater extent than if the wire 1202 were entirely constrained by a tube (e.g., if there were no gap 1230 and the first and second tubes 1210, 1220 were connected to form a single tube). In the illustrated example, the gap 1230 permits the wire 1202 to flex outside of a front profile of the retractor blade 1200. This added room to flex can ease the transition of the wire 1202 from the relatively straight first tube 1210 to the curved second tube 1220. The easing of the transition can reduce a likelihood of the wire 1202 binding or breaking during insertion. Although the illustrated example includes tubes, other structures can be used to direct or redirect the path of the wire 1202, other structures can be used. Further, while the illustrated gap 1230 is illustrated as an absence of material, it need not be. For example, the gap 1230 between the first and second tubes 1210, 1220 can be formed from a tube having an increased diameter relative to the other tubes 1210, 1220. In yet another example, the gap 1230 can be formed from a section of a material being more flexible or stretchy than the material from which the other tubes 1210, 1220 are constructed from. For instance, the gap 1230 can be defined in any of a variety of ways in which permit additional movement, bending, or flexibility of a portion of the wire 1202 within the gap 1230 relative to the portions of the wire 1202 with in the tubes 1210, 1220. The gap 1230 can be a section that is less constraining of the wire 1202 than the other sections defined by the tubes 1210, 1220.

Wire inserters and wire removers may be utilized to insert and remove wires to and from use in a surgical space. A wire inserter can be configured to guide a wire along a controlled path for insertion into bone. A wire remover can be configured to grip and remove a surgical wire from hard bone.

An inserter can facilitate changing an angle of a wire (e.g., relative to a retractor blade, relative to the patient's skin, or relative to an operative corridor) from an initial insertion angle to an angle along which the wire will be inserted into, for example, a vertebral endplate. The changing of the angle can be beneficial because surgical corridors used in minimally invasive surgery can be relatively constrained, which can limit the ability of a user to both insert the wire down the corridor and angle the wire into a desired anatomical structure. The guides can facilitate the changing of the direction of the K-wire.

The inserter can be so configured via a fixed or expandable pathway to accommodate the trajectory of the wire. Further, the inserter can protect both the wire and patient tissue during insertion, whether insertion is achieved with or without power. The inserter can include features to guide fixation instruments and the one or more features can vary in shape and size for achieving desired trajectory and ease of insertion.

A wire remover may be configured to remove the surgical wire even if it is bent. The surgical wire can be inserted into the wire remover, such as by top loading the wire remover or by side loading the remover. In many examples, once the surgical wire is placed in the remover, the wire does not need to be reloaded into the remover. The wire remover can be configured to removes the surgical wire in a controlled fashion. The wire remover can leverage against a retractor, retractor blade, table arm, or other structure to facilitate removal. The wire remover can push or pull the surgical wire a particular distance each time the remover is activated (e.g., its handles are squeezed toward each other). The wire remover can be configured to remove the wire in a single or multiple activations. The wire remover can be configured to remove the surgical wire from both the patient's bone and a surgical shim or surgical retractor through which the wire extends. The wire remover can be configured to grip and control the surgical wire to resist the wire from springing aggressively (e.g., springing aggressively within a surgical access corridor or near a person's face). The surgical wire remover can be configured for use in an operating room. The surgical wire can be cleanable (e.g., sterilizable) and able to be dismantled.

While wire pullers exist in other industries, the surgical use case presents specific challenges that limit the ability of wire pullers from other industries being used in surgery. For example, such pullers may be unable to be safely or repeatedly sterilized and may be unable to sufficiently handle the specific characteristics of a surgical wire, among other differences that will be apparent from this disclosure. Some modifications to wire pullers disclosed herein include mechanisms having improvements in gripping and pulling a surgical wire, one or more retainment features that resist the surgical wire from walling out, and the surgical wire remover being configured for leveraging against a structure in an operating room, among others.

Figure 13:
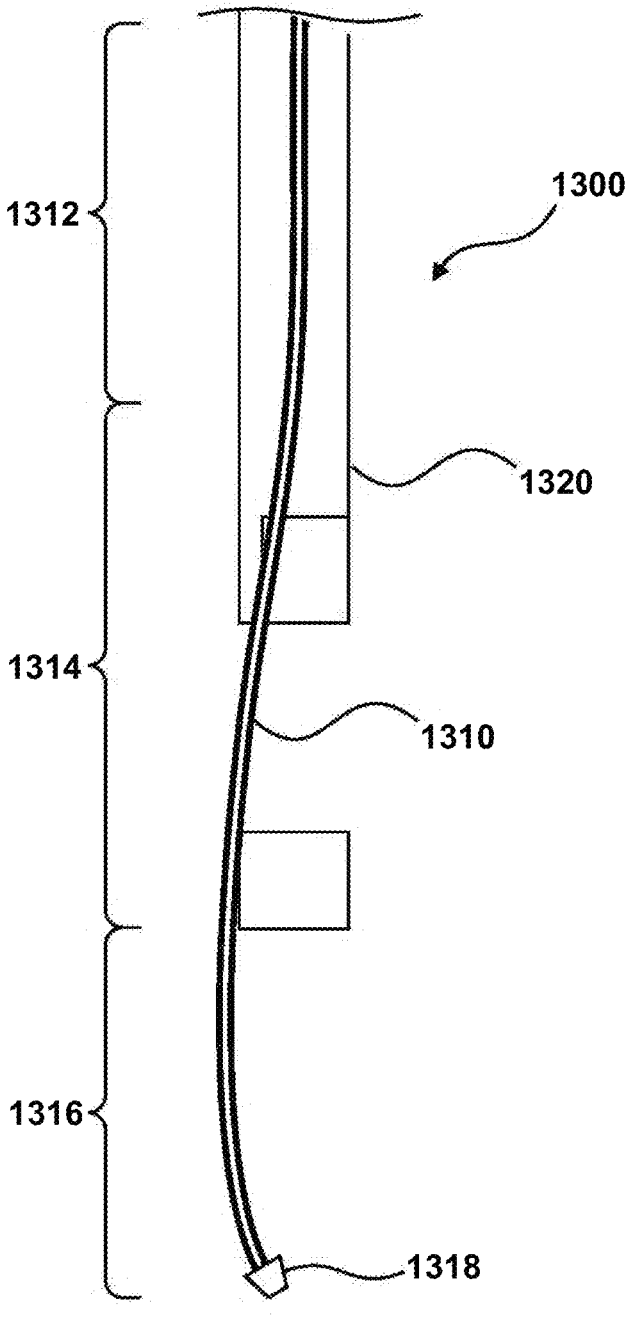
FIG. 13 is a schematic view of an illustrative inserter.

FIG. 13 illustrates an example guided inserter 1300 for a surgical wire. The inserter 1300 is a component configured to direct a surgical wire through a guide of a shim that can be coupled to a retractor blade (e.g., a retractor blade as discussed herein or other suitable retractor blade). As illustrated, the inserter 1300 includes a guide tube 1310 having a tip 1318 and being coupled to a frame 1320. The guide tube 1310 can be constructed from or coated in a material to reduce friction as the wire moves through the guide tube 1310. The inserter 1300 can be configured for use in any of a variety of ways. For example, the inserter 1300 can be configured to be integral with a shim inserter (e.g., the inserter 1300 is coupled to the shim inserter in such a way that the inserter cannot be non-destructively removed). In another example, the inserter 1300 can be a separate component that is couplable to a shim inserter. In further examples, the inserter 1300 is a standalone component not configured to be coupled to another device.

In some examples, the guide tube 1310 extends along the entire length of the retractor blade to which the inserter 1300 is coupled such that a proximal opening of the tube 1310 is disposed at a proximal end of the retractor blade. In other examples, the proximal end of the guide tube 1310 extends along the length of the shim, such that the proximal end of the guide tube 1310 is disposed at the proximal end of the shim.

As illustrated, the guide tube 1310 includes a first section 1312, a second section 1314, and a third section 1316. The first section 1312 is a portion of the guide tube 1310 running substantially parallel to a length of the inserter 1300 (and a length of the shim and the retractor blade when the inserter 1300 is coupled thereto). The second section 1314 is a portion of the guide tube 1310 configured to curve the wire away from an ultimate direction in which the wire will extend. The third section 1316 is a section of the tube 1310 configured to curve the wire toward the ultimate direction in which the wire will extend. The curving of the sections can facilitate changing the direction of the wire. Further, the sections can facilitate resisting movement of the shim and retractor blade relative to the wire.

The tip 1318 can be a portion configured to interface with the guide of the shim. For example, the tip 1318 can be a portion configured to fit within a proximal end of the guide to facilitate alignment of the tube 1310 and the guide such that the wire can transition from the guide tube 1310 into the guide.

The frame 1320 can provide support to the guide tube 1310 and hold the sections 1312, 1314, 1316 in a desired position. The frame 1320 can further be configured to couple the inserter 1300 to the shim or retractor blade, such as via any of a variety of couplers, such as clips, tabs, magnets, other couplers, or combinations thereof.

In the illustrated example, the guide tube 1310 is a gently curving tube sized to accommodate the wire. The guide tube 1310 can be sufficiently stiff so as to change the direction of the wire and resist unwanted movement of the guide tube 1310 due to forces of the wire.

Figure 14:
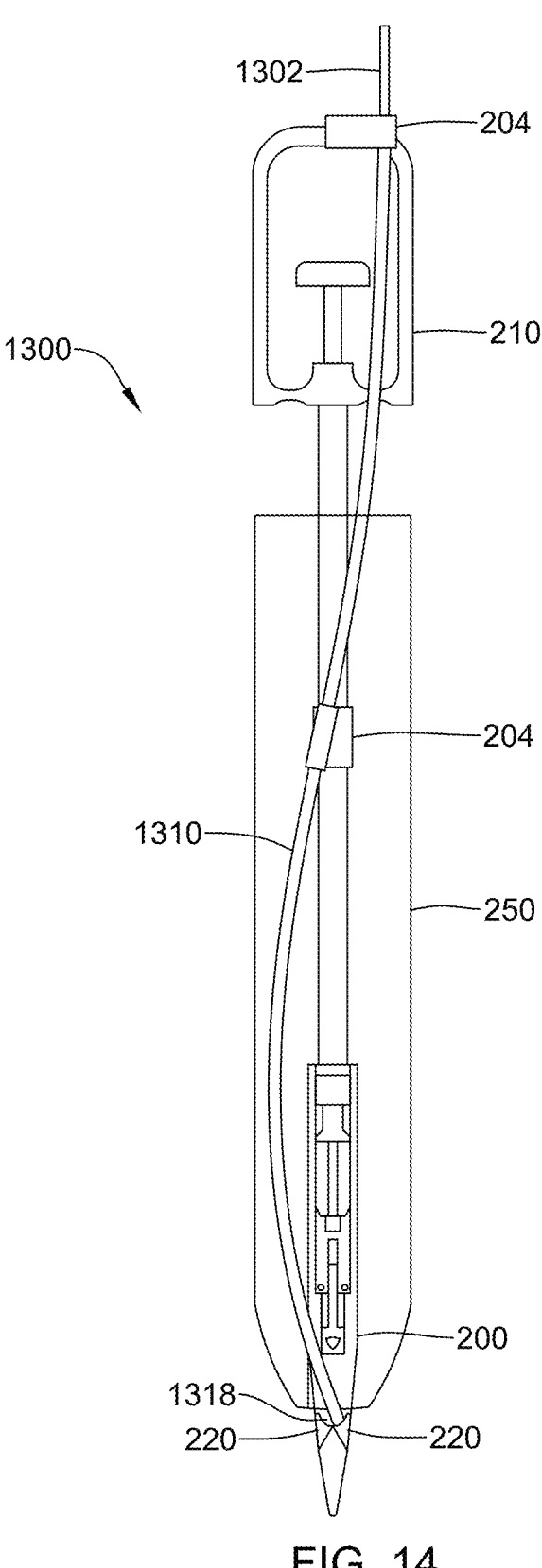
FIG. 14 is a schematic view of the illustrative inserter depicted in FIG. 13, coupled to a retractor blade and having the tip disposed in a guide of a shim.

FIG. 14 illustrates an example implementation of the inserter 1300 coupled to a shim inserter 210 used to insert a shim 200 into a retractor blade 250. As illustrated, the inserter 1300 is coupled to the shim inserter 210 such that the shim inserter 210 acts as the frame 1320. The couplings 204 can take any of a variety of forms including clips, brackets, other couplings, or combinations thereof.

The tip 1318 of the guide tube 1310 is disposed in one of two guides 220 in the shim 200.

Bends of the guide tube 1310 occur primarily within a plane parallel to the length and width of the shim 200 and retractor blade 250. In addition or instead, the tube 1310 can include substantial movement in a third direction (e.g., in a direction parallel to a thickness of the shim 200 and retractor blade 250). The three-dimensional movement can beneficially resist movement of the shim 200 and retractor blade 250 relative to the guide tube 1310 or a patient's anatomy.

Figure 15:
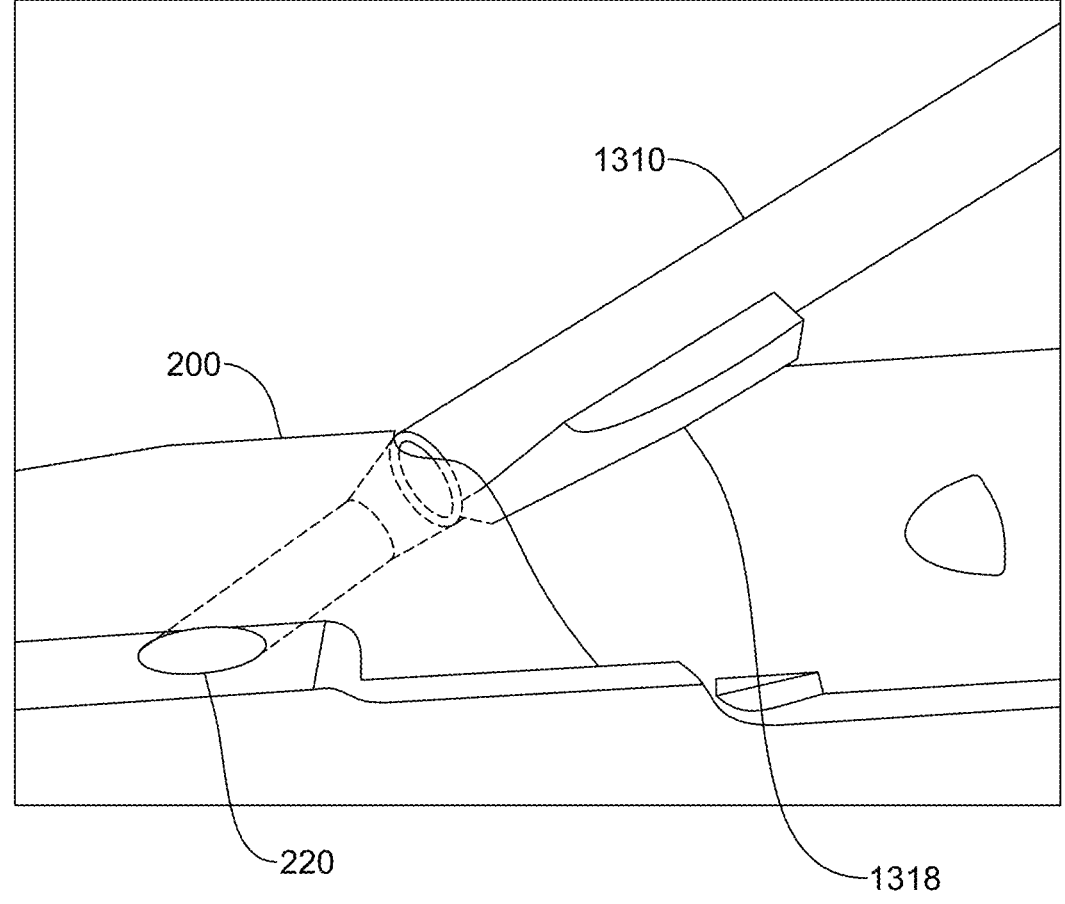
FIG. 15 is a schematic perspective view of an illustrative connection between the distal end of a guide tube and the guide of the shim depicted in FIG. 14.

FIG. 15 illustrates an example perspective view of a connection between the distal end of the guide tube 1310 and the guide 220 of the shim 200. In this example, the tip 1318 is an offset tip feature configured to mate with a portion of the guide 220 to facilitate a connection between the guide 220 and the inserter 1300.

Figure 16:
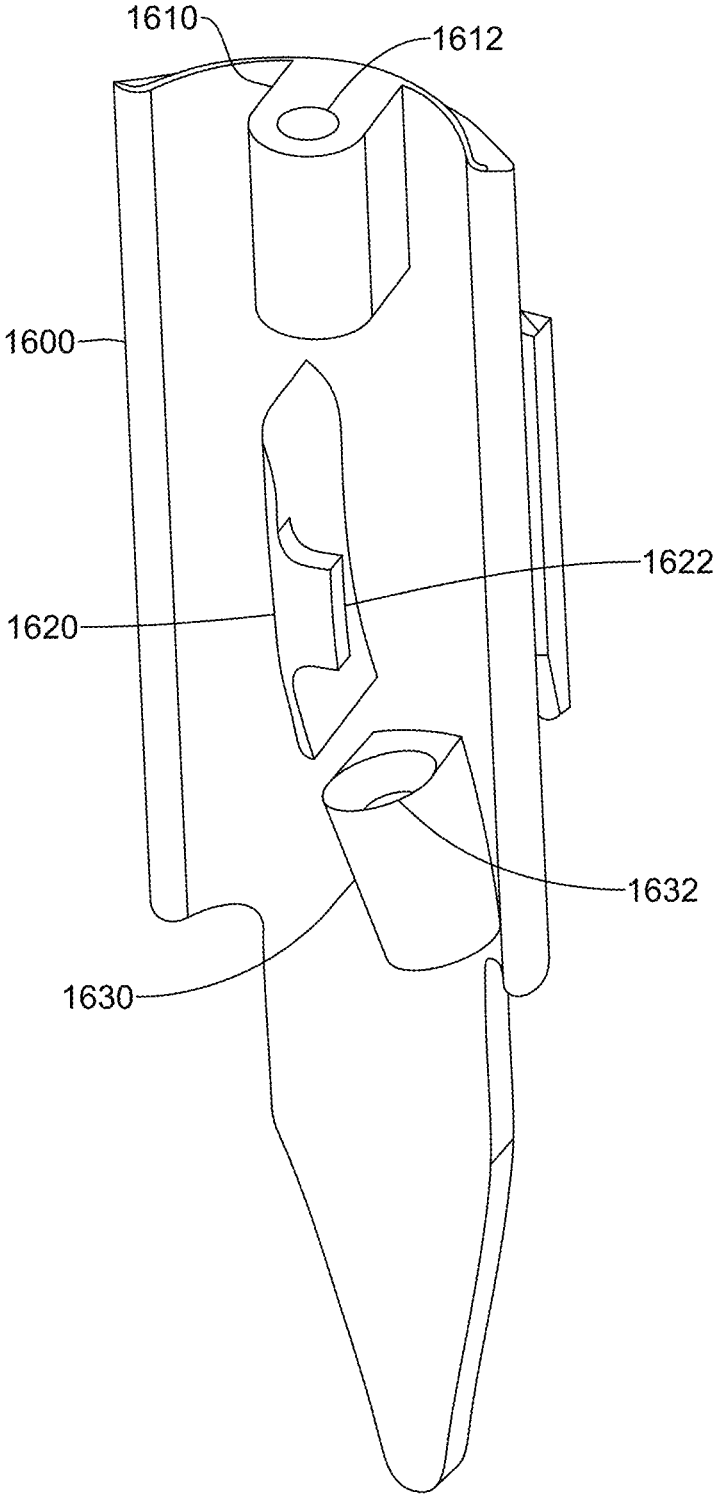
FIG. 16 is a schematic perspective view of an illustrative shim having built in features for receiving a wire at a first trajectory and redirecting the wire to exit along a second trajectory.
Figure 17:
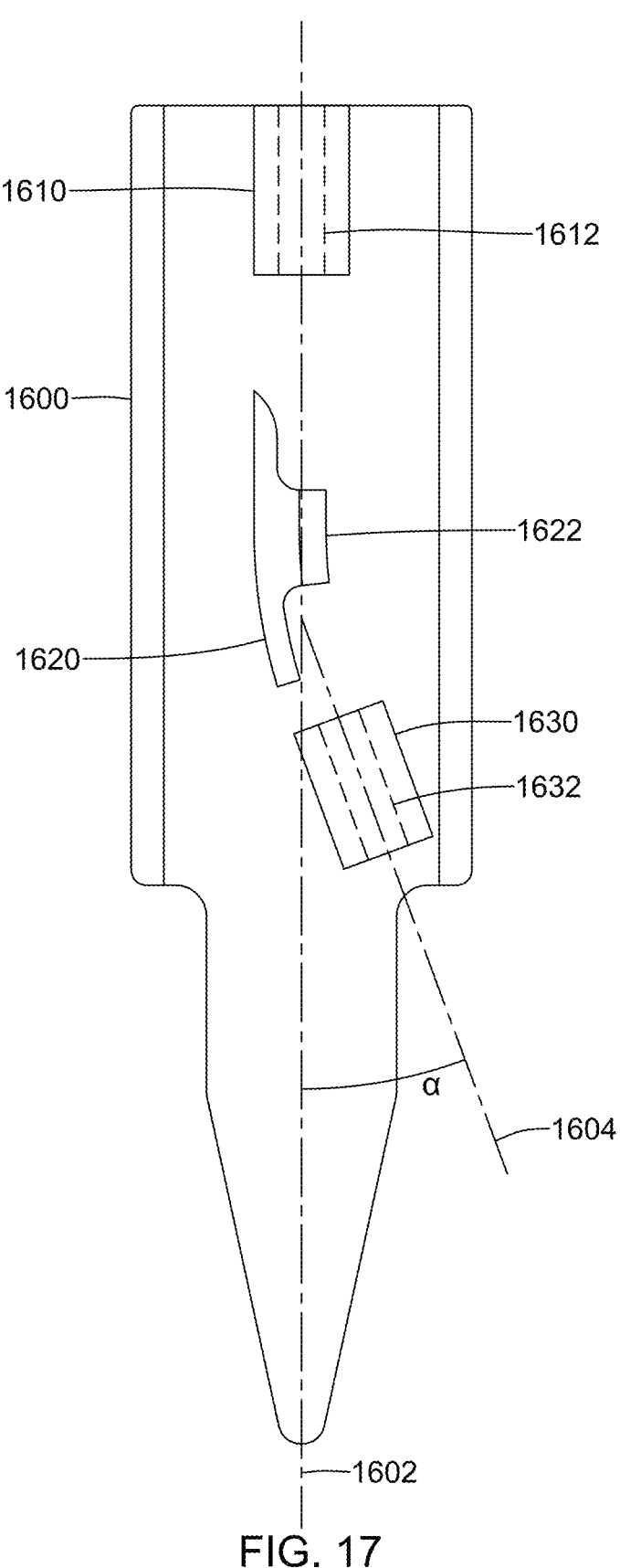
FIG. 17 is a schematic front view of the illustrative shim of FIG. 16.

FIGS. 16 and 17 illustrates an example, shim 1600 having built in features for receiving a wire at a first trajectory and redirecting the wire to exit along a second trajectory. As illustrated, the shim 1600 includes a first guide 1610, a second guide 1620, and a third guide 1630. The first guide 1610 includes a first guide channel 1612 configured to receive and direct a wire along a first trajectory 1602 (see e.g., FIG. 17). The third guide 1630 includes a third guide channel 1632 configured to receive and direct a wire along a second trajectory 1604 (see e.g., FIG. 17). The second guide 1620 includes second roof 1622 and is configured to redirect the wire from the first trajectory 1602 to a second trajectory 1604.

The first guide channel 1612 and the third guide channel 1632 can be enclosed channels or tunnels through material. The first guide channel 1612 and the third guide channel 1632 can define funnel shaped areas to facilitate the collection and direction of the wire into a more constrained section.

The second guide 1620 can be a component having one or more curves configured to change the direction of the wire. For example, the second guide 1620 can be configured to cause an incoming wire to skive, deflect, curve, or otherwise change directions toward the third guide 1630.

The guides 1610, 1620, 1630 can not only serve to guide the wire, but also to provide an interface between the wire and the shim 1600 such that, once the wire is implanted (e.g., in a patient's vertebral endplate), relative movement between the wire and the shim 1600 is resisted.

FIG. 18 illustrates an example method 1800 of using a wire during a spinal procedure. In an example, the procedure is a lateral interbody fusion procedure performed while the patient is in a prone position, but the techniques herein can be applicable to other procedures, including, lateral interbody fusions, transforaminal interbody fusions, anterior lumbar interbody fusions, posterior interbody fusions, procedures at the cervical spine, procedures at the thoracic spine, procedures at the lumbar spine, procedures while the patient is in the prone position, procedures while the patient is in the supine position, procedures while the patient is in a lateral decubitus position, other procedures, or combinations thereof. The method can begin with operation 1802.

Operation 1802 includes making components available for use. The component can include any of the components described elsewhere herein, such as a retractor (e.g., having retractor blade 250), a shim (e.g., shim 200 or shim 1600), and an inserter (e.g., inserter 1300), among others, variations thereof, and combinations thereof. In some examples, making available for use includes providing the parts of the components. The operation 1802 can include removing such components from sterile packaging and arranging them for use in an operating room.

Operation 1810 includes, during the spinal procedure, placing a retractor in a target surgical location. The surgical location can be, for example, an intervertebral disc space at a spinal level where a procedure is to be performed. In an example, the operation 1810 can include advancing one or more blades of the retractor (e.g., blade 250) over a dilation system such that a center retractor blade is the posterior most blade of the retractor. Following operation 180, the flow of the method 600 can move to operation 1812.

Operation 1812 includes attaching a shim to the retractor blade. For example, the shim can be coupled to a shim inserter that is used to facilitate attaching the shim to the retractor blade. In some examples, the shim inserter can double as a wire inserter. For example, the same device used to attach the shim to the retractor blade can be used to insert the wire. The shim can be placed at a proximal location of the retractor blade and moved distally along a blade track of the retractor blade. The blade track can include dove tail grooves formed on the interior of blade that accommodate the tabs along the shim. Following operation 1812, the flow of the method 1800 can move to operation 1814.

Operation 1814 includes advancing the shim into the disc space. For example, the shim is advanced along the retractor blade until the distal end of the shim pierces the disc. The shim continues to be advanced into the disc space such that the barb (if any) is fully within the disc. The shim can be advanced such that a distal opening of a guide is within the disc. Following operation 1814 the flow of the method 1800 can move to operation 1815 or 1816.

Operation 1815 includes attaching the inserter 1300. For example, the operation 1815 can include coupling the frame 1320 to one or both of the retractor blade 250 and the shim 200. The coupling can be achieved using any of a variety of techniques depending on the construction of the components. In an example, the frame 1320 is coupled to both the retractor blade 250 and the shim 200. In addition, attaching the inserter 1300 can include disposing the distal end of the guide tube proximate a guide of the shim 200. Following operation 1815, the flow of the method 1800 can move to operation 1816.

Operation 1816 includes advancing a wire into a proximal opening of the shim guide 220. In some examples, the wire is advanced into the opening via the guide tube 1310. For example, the wire is first inserted into a proximal end of the guide tube 1310, advanced through the guide tube 1310, advanced out of the distal end of the guide tube 1310, and into and through the guide 220. This can include advancing the wire along a straight section of the guide tube 1310, bending a portion of the wire away from the guide 220, and then bending the wire toward the guide 220. In further examples, the wire is advanced through the first guide channel 1612, the wire is redirected using the second guide 1620, and advanced into the third guide channel 1632. During the advancing, the wire can be bent such that a distal portion of the wire changes from advancing along the first trajectory 1602 to advancing along a second trajectory 1604.

Operation 1818 includes advancing the wire through the guide 220. The advancing the wire through the guide 220 can include causing or permitting the guide 220 to bend the wire such that the distal end of the wire follows a guide axis, such as by bending the wire. In other examples, the guide 220 does not substantially change the direction of the wire but instead maintains a general trajectory of the wire.

Operation 1820 can include advancing a distal end of the wire out of a distal opening of the guide. In many examples, the wire exits the distal opening and directly enters the disc. In other examples, the wire does not directly enter the disc. Following operation 1820, the flow of the method 1800 can move to operation 1822.

Operation 1822 can include advancing the distal end of the wire into a vertebral endplate. Sufficient amounts of the wire can be advanced into the vertebral body to facilitate securing the shim and thereby secure the retractor blade coupled to the shim. In this manner, the wire resists movement of the coupled blade, such as posteriorly towards nerve tissue located in the posterior portion of the psoas muscle. Following operation 1822, the flow of the method 1800 can move to operation 1824.

Operation 1824 can include expanding the operative corridor with a retractor (e.g., a retractor as discussed herein or other suitable retractor). For example, retractor blades of the retractor are separated, providing an operative corridor through which instruments or implants can be advanced to the target site. Following operation 1824, the flow of the method 1800 can move to operation 1826.

Operation 1826 can include performing one or more procedures through the operative corridor. Any number of procedures may be performed on the spine through the lateral access corridor, such as a fusion procedure, a total disc replacement, or a corpectomy, among other procedures.

After a user is finished using the wire, the user can use a wire remover to grip and remove the wire. An example wire remover uses cam action to secure the wire for removal. The wire remover can be configured to facilitate removal of a partially implanted wire in a controlled, measured manner. The wire remover can include a surface configured to use an access instrument (e.g., a retractor, an A-arm, or a frame) for leverage. The wire remover can include at least one lever for mechanical advantage for the removal of a fixation instrument. The wire remover can include a feature that contains the fixation instrument, leading into a channel on the instrument.

The wire remover can be configured for use in an operating room, such as by being made from material suitable for being sterilized. The wire remover can be provided in a sterile manner. The wire remover can be provided as part of a surgical kit. The wire remover can be configured for use with gauges of wire commonly found in operating rooms. The wire remover can be used within an operating room during a surgical procedure.

Figure 19:
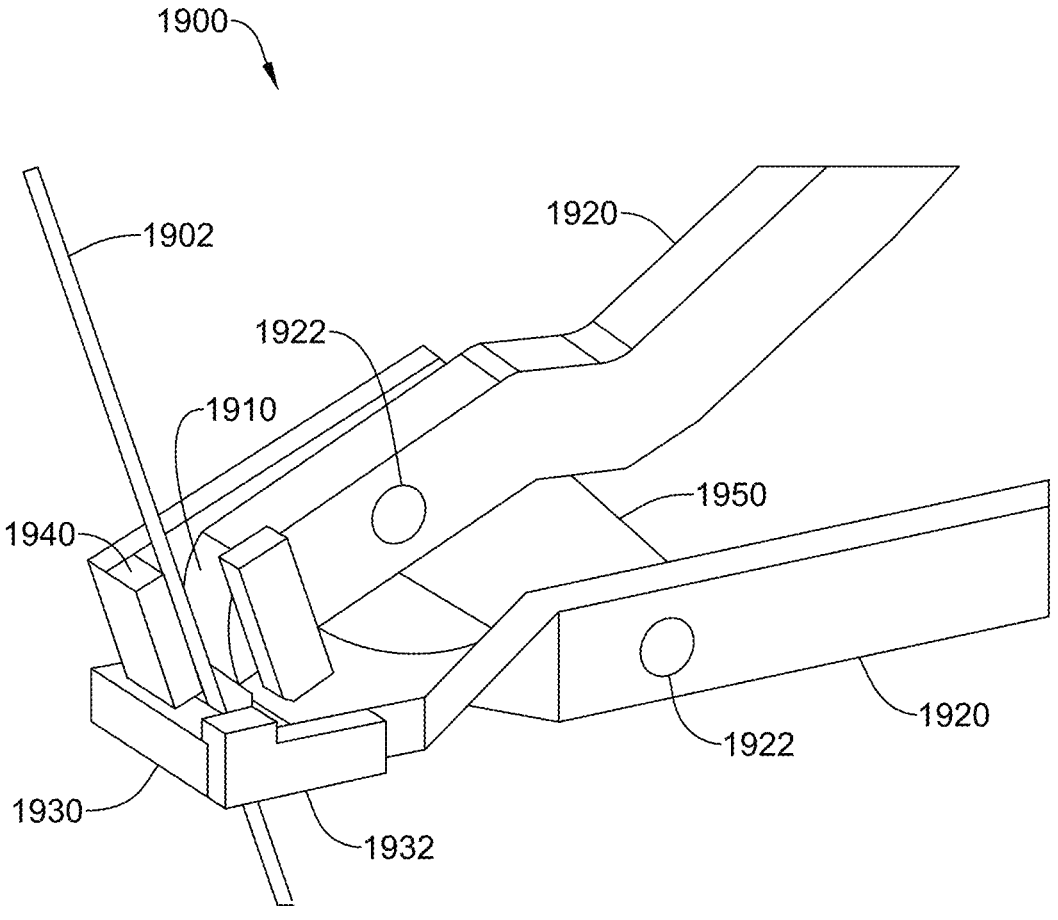
FIG. 19 is a schematic view of an illustrative wire remover for removing a wire.

FIG. 19 illustrates a first example wire remover 1900 for removing a wire 1902. As illustrated the wire remover includes a grip surface 1910 coupled to a first arm 1920, a base 1930 coupled to a second arm 1920. The arms 1920 are linked by a link 1950 and pins 1922 (e.g., pivots). The link 1950 is further ultimately coupled to a plate 1940. A guard 1932 can be permanently, removably, movably, or pivotally coupled to the base 1930.

The grip surface 1910 is a portion of the wire remover 1900 configured to interact with the wire during use of the wire remover 1900. As illustrated, the grip surface 1910 is curved, which can facilitate use of the grip surface 1910 with respect to various sizes of wires 1902. The grip surface 1910 can include one or more surface features configured to increase an amount of grip or bite the grip surface 1910 has against the wire 1902. Such features can include knurling, teeth, other features, or combinations thereof.

The arms 1920 are elongate structures that facilitate use of the inserter by the user. The arms 1920 can include grip sections to facilitate gripping by the user.

The link 1950 is a series of one or more components that couple one or more other components of the remover 1900. For example, as illustrated in FIG. 19, the second arm 1920 is coupled to the link 1950 via the pin 1922. The link 1950 is also coupled to the first arm 1920 via another pin 1922. The pins 1922 can be implemented via any of a variety of techniques, such as pivot pins. In some implementations, one or more of the pins 1922 can be replaced with a component that rides in a track (e.g., a track defined by the link 1950). In some examples, one or both of the arms 1920 can include one or more clips or other retaining features to hold a proximal end of the surgical wire 1902 to keep the surgical wire out of the surgeon's way. In an example, the handles (or a silicone cover thereof) can include one or more pockets configured to receive and retain the surgical wire. In an example, one or both of the arms 1920 can be detachable.

The base 1930 is a component coupled to or integral with the second arm 1920. The base 1930 can define or more openings or slots configured to receive the wire 1902 during use of the remover 1900. The base 1930 can also be configured to act as a pivot or leverage point that is configured to interact (e.g., press against) with another structure (e.g., a proximal end of a retractor) during use. In some examples, the base 1930 includes one or more features for interacting with a retractor. For example, the base 1930 can include one or more protrusions, features, or mechanisms configured to hook onto or otherwise secure the wire remover 1900 to the retractor. In some examples, the wire remover 1900 includes one or more mechanisms that grip onto the retractor as the grips are squeezed (e.g., by pinching a portion of the retractor between two surfaces of the inserter). In some examples, the base 1930 is relatively thick to allow the user to better push off the retractor surface. For example, the base 1930 can be thicker than a thickness of the arm 1920. The base 1930 can extend below a bottom of the arm 1920 when the base 1930 abuts a retractor.

A guard 1932 can be permanently, removably, movably, or pivotably coupled to the base 1930 to block or permit selective access to an opening in the base 1930. The guard 1930 can be configured to encourage the surgical wire to remain workably disposed in the remover 1900.

The plate 1940 is a portion against which the wire 1902 is urged during use of the remover 1900. As illustrated, the plate 1940 is coupled to or integral with the link 1950. The plate 1940 can include one or more surface features configured to increase an amount of grip or bite the plate 1940 has against the wire 1902. Such features can include knurling, teeth, other features, or combinations thereof. The plate 1940 can be positioned such that there is a gap between the plate 1940 and the grip surface 1910 when the remover 1900 is in a first configuration (e.g., an unsqueezed configuration) sized to accommodate the wire 1902. When the remover 1900 is in or is transitioned into a second configuration (e.g., a squeezed configuration), the gap between the plate 1940 and the grip surface 1910 is reduced. For example, the reduction can be because the grip surface 1910 is moved toward the unmoving plate 1940, because the plate 1940 is moved toward the unmoving grip surface 1910, or both the grip surface 1910 and the plate 1940 move.

Figure 20:
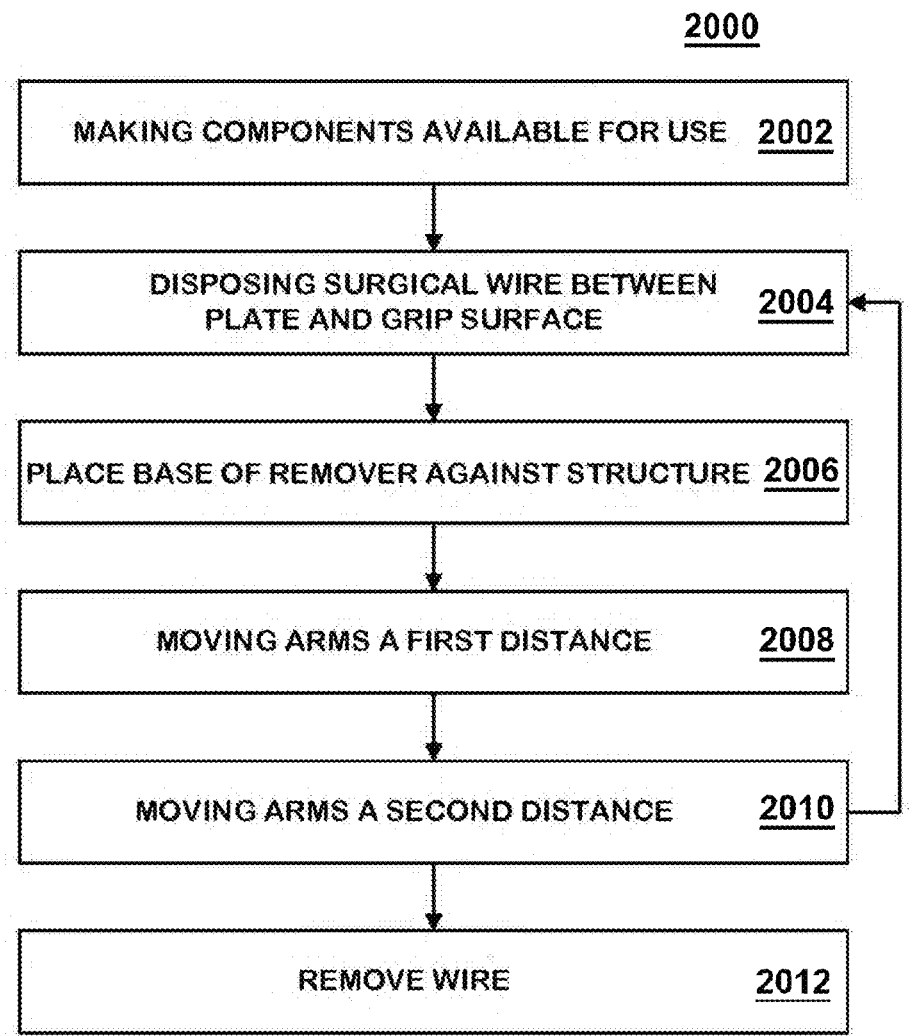
FIG. 20 is a schematic diagram of an illustrative method of using a wire remover.

FIG. 20 illustrates an example method 2000 of using the wire remover 1900. The method can begin with operation 2002. In some examples, operation 2002 can follow operation 1826, which is described above.

Operation 2002 includes making components available for use. The component can include any of the components described elsewhere herein, such as the wire remover 1900. In some examples, the wire remover 1900 is provided in an unassembled state and the wire remover 1900 is assembled as part of this operation 2002. In other examples, the wire remover 1900 is provided in an assembled state. In some examples, making available for use includes providing the parts of the components. The operation 2002 can include removing components from sterile packaging and arranging them from use in an operating room. Following operation 2002, the flow of the method 2000 can move to operation 2004.

Operation 2004 includes disposing the wire 1902 between the plate 1940 and grip surface 1910 of the wire 1902. The wire 1902 can be a wire having a distal end at least partially embedded into a bone of a patient. This can include disposing the wire 1902 such that the wire 1902 extends between the plate 1940 and grip surface 1910 and through an opening in the base 1930. This can include, for example, extending the wire through the opening in the base 1930 and advancing the remover 1900 along the wire 1902 until the bottom of the base 1930. Alternatively, the wire 1902 can be side loaded into the remover 1900, such as by moving the guard 1932 out of the way of the slot in the base 1930, laterally moving the remover 1900 over the wire. Where the remover 1900 includes a guard 1932, the operation 2004 can include opening the guard 1932 to accept the wire 1902 and then closing the guard 1932 after disposing the wire 1902 between the plate 1940 and the grip surface 1910. Following operation 2004, the flow of the method 2000 can move to operation 2006.

Operation 2006 includes placing the base 1930 against a structure. In many examples, the structure is a retractor, but it can be another structure suitable to leverage off of, such as an arm coupled to a surgical table or a robot. The operation 2006 can include sliding the remover 1900 down the wire 1902 until the bottom of the base abuts a proximal portion of the structure. Following operation 2006, the flow of the method 2000 can move to operation 2008.

Operation 2008 includes moving the arms 1920 toward each other a first distance, such as by a user manually squeezing the arms 1920 together. Due to the mechanical structure of the remover 1900, this movement across the first distance can initially cause the grip surface 1910 to urge against the wire 1902 and press the wire 1902 against the plate 1940. This force can resist movement of the wire 702 relative to the grip surface 1910. Following operation 2008, the flow of the method 2000 can move to operation 2010.

Operation 1010 includes moving the arms toward each other a second distance beyond the first distance, such as by the user manually squeezing the arms 1920 together. In some examples, substantive further pinching of the wire 1902 between the plate 1940 and the grip surface 1910 is not possible and this resistance of movement causes the link 1950 to cause the mechanisms of the remover 1900 to move such that the plate 1940 and grip surface 1910 move away from the base 1930. Because the wire 1902 is held between the plate 1940 and grip surface 1910, the movement away from the base 1930 can cause the wire 1902 to be pulled. For example, where the base 1930 is held against the retractor, the base 1930 is prevented from moving distally. These movements and constraints can cause the wire 1902 to be pulled out of the anatomical structure into which it was inserted.

In some examples, the first squeeze of the arms 1920 is sufficient to pull the wire 1902 from the anatomical structure. In which case, the flow of the method 2000 can move to operation 2012 in which the user continues to squeeze the arms to hold the wire 1902 and remove the wire from the operative corridor. In other examples, the first squeeze is insufficient. In such a case, the arms are allowed to spread apart, the base 1930 is again brought against the retractor blade and the above process (e.g., of squeezing, choking up on the wire, and squeezing again) is repeated again until the wire 1902 is removed. In such an example, the flow of the method 2000 can return to operation 2004.

Figure 21:
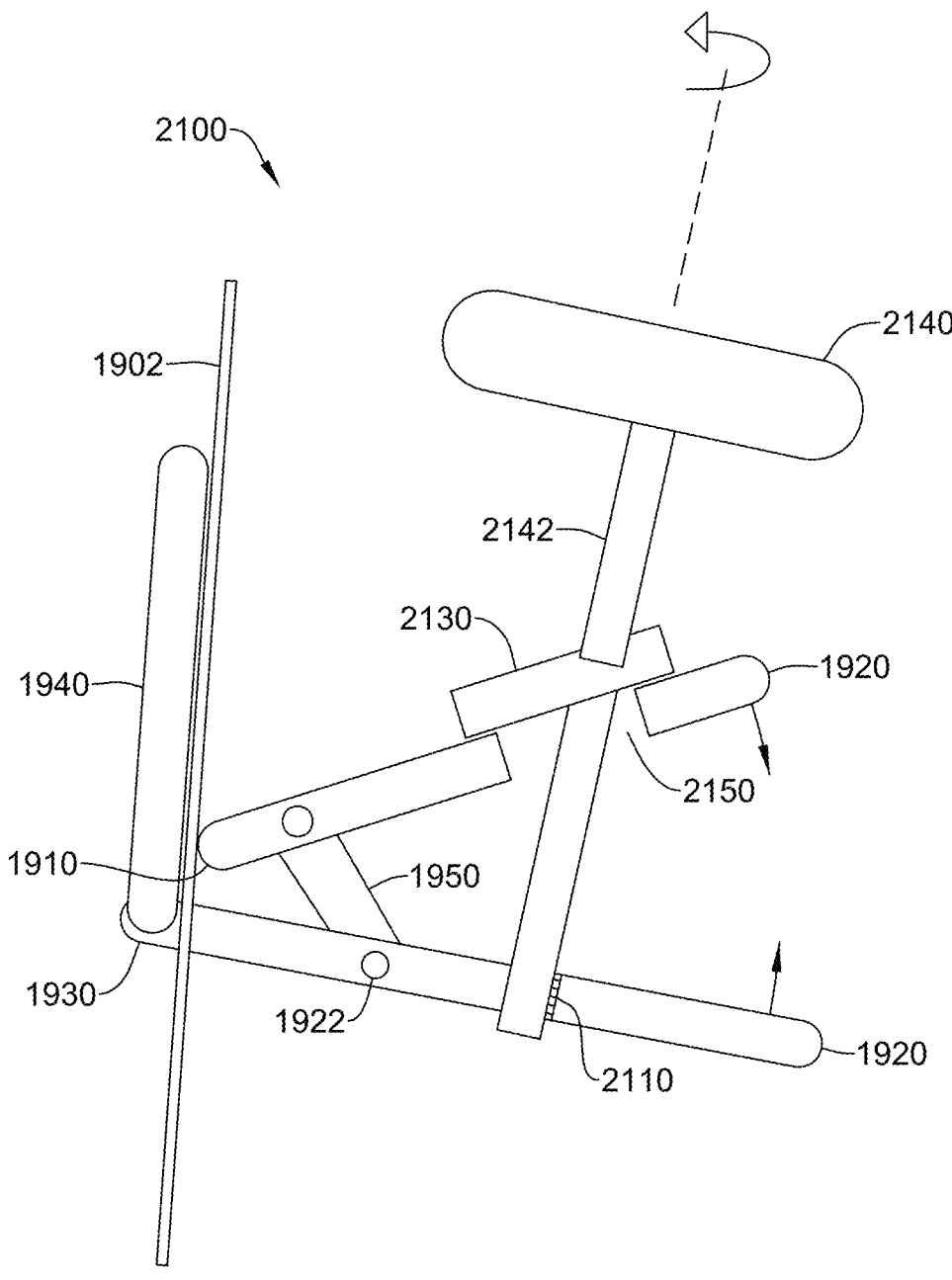
FIG. 21 is a schematic view of an illustrative surgical wire remover.

FIG. 21 illustrates an example surgical wire remover 2100 that includes one or more modifications relative to remover 1900. In particular, the second wire remover 2100 includes a feature for providing mechanical advantage. In the illustrated example, there is a threaded interface 2110 in one arm 1920 and a slot 2150 in the other arm 1920 such that a threaded, swivel head bolt 2130 can be attached and actuated with a handle 2140 (e.g., which can be a ratcheting T-handle) to improve the mechanical advantage compared to squeezing the arms 1920 by hand. In other examples, mechanical advantage can be provided by a threaded rod extending through the slot 2150 and coupled to the other arm 1920 via a hinged connection. The handle 2140 can include a threaded opening such that the handle 2140 can be threaded onto the rod, and pushed down on the arm 1920. In still further examples, the remover 2100 can include a mechanism that resists compressed arms 1920 from spreading back apart, such as a ratcheting structure.

In some examples, the handle 2140, bolt 2130, and a joining shaft 2142 between the handle 2140 and the bolt 2130 can be removed or simply not used. When the handle 2140, the bolt 2130, the joining shaft 2142, or combinations thereof are removed or not used, the wire remover 2100 can be used with simple hand actuation without added profile or weight, while still having the flexibility of adding the handle 2140, bolt 2130, and joining shaft 2142 if desired.

In some implementations, one or more features of a remover 1900, 2100 can be used to implement an inserter, such as by positioning the remover 1900, 2100 such that its force is used to push the wire 1902 in rather than pull it out.

Figure 22:
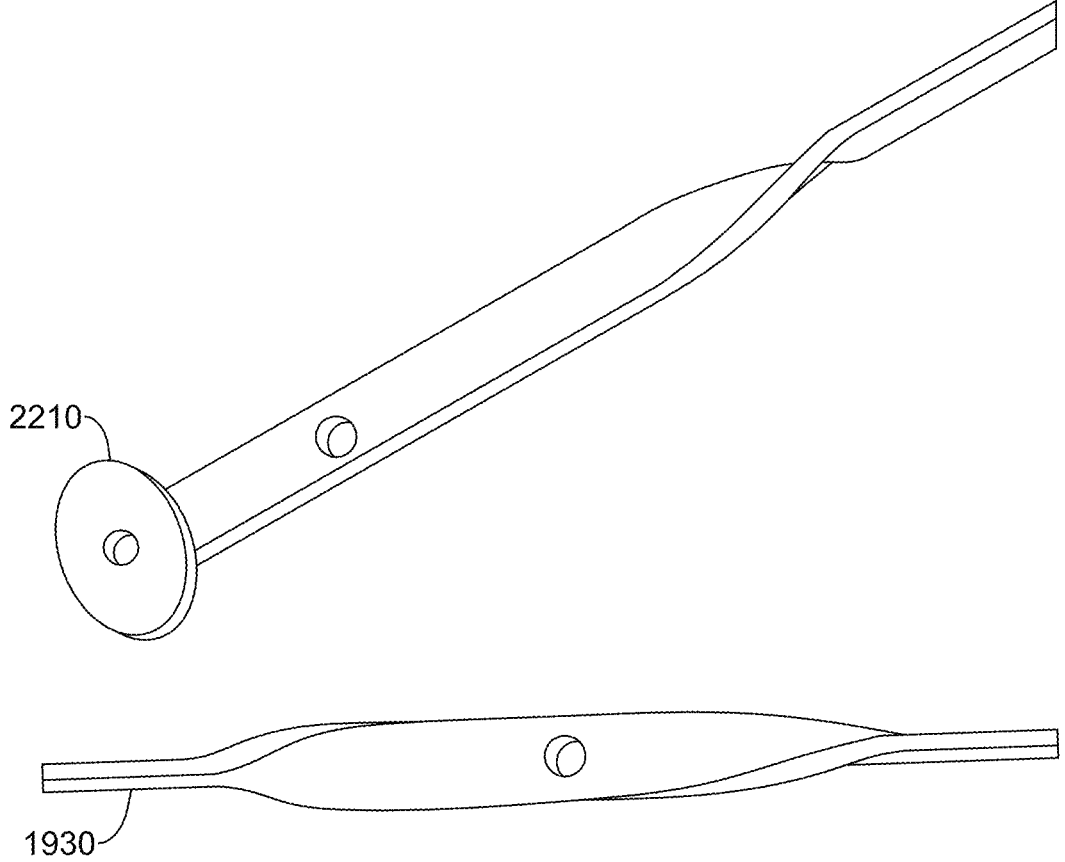
FIG. 22 is a schematic view of an illustrative grip surface.

FIG. 22 illustrates an example alternative grip surface 2210 having an offset cam structure that can be used with wire removers herein to provide additional mechanical leverage.

Figure 23:
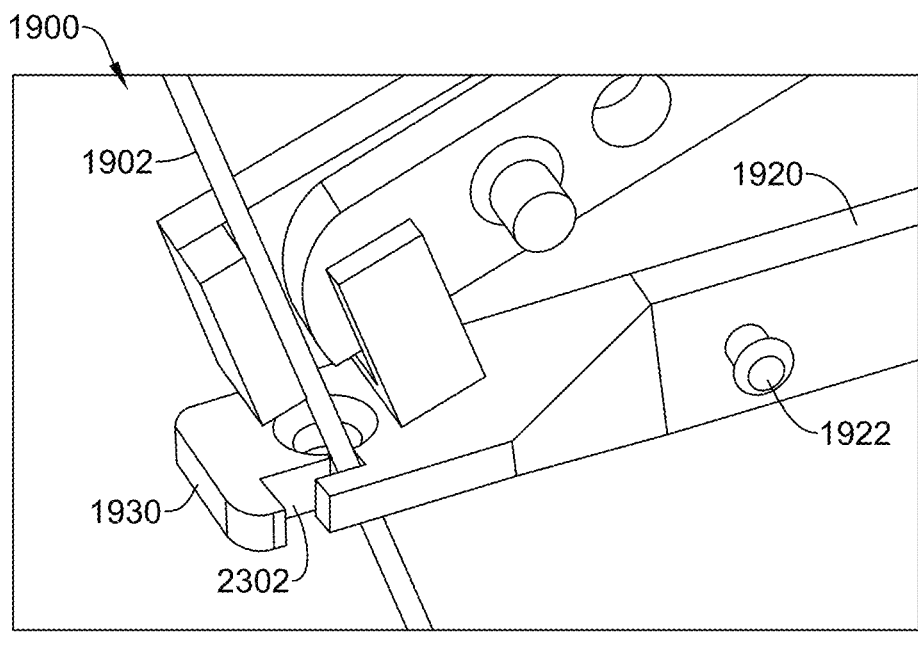
FIG. 23 is a schematic view of an illustrative path having a boxy S-shape.
Figure 24:
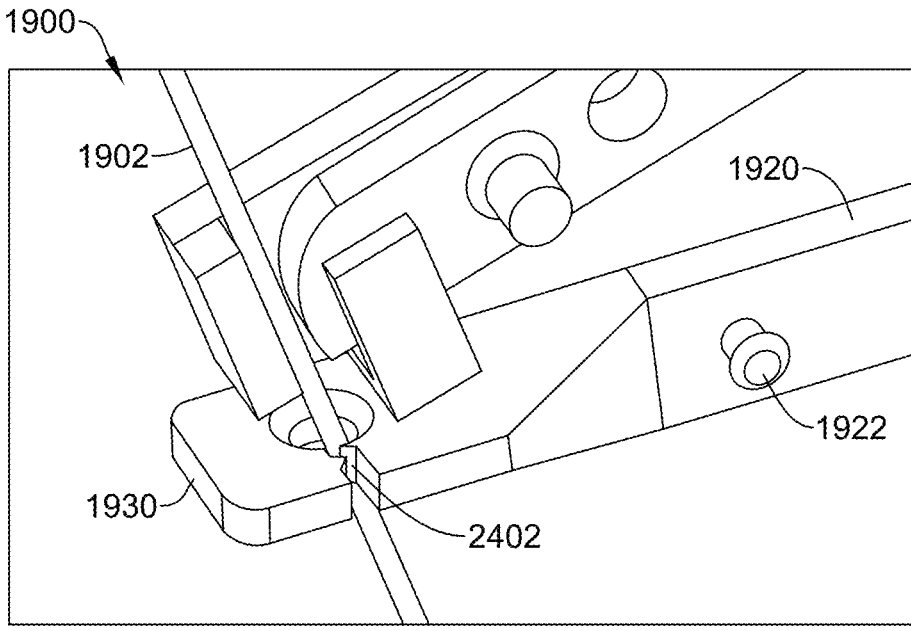
FIG. 24 is a schematic view of an illustrative path having multiple protrusions into the path.

FIGS. 23 and 24 illustrate example wire removers 1900 having bases 1930 with side loading paths 2302, 2402 configured to permit the lateral insertion of the surgical wire 1902 while resisting unwanted removal of the surgical wire 1902. The paths can be configured to increase the difficulty of laterally removing the surgical wire from the base (and, in many implementations increase the difficulty of passing the surgical wire into the path to reach the base).

FIG. 23 illustrates a first path 2302 having a boxy S-shape such that the surgical wire must be moved in a first direction to enter the path, in a second direction to continue through the path, and then in the first direction again to reach the working aperture of the base 1930. In addition, the width of the first path 2302 is relatively close to the thickness of the surgical wire such that it is relatively difficult to move the surgical wire into the path. These features can cooperate to decrease the likelihood of inadvertent removal of the surgical wire from the working aperture of the base 1930.

FIG. 24 illustrates a second path 2402 having multiple protrusions into the path 2402 that must be navigated around to reach the working aperture of the base 1930. Like the first path 2302, the width of the second path 2402 is relatively close to the thickness of the surgical wire such that it is relatively difficult to move the surgical wire into the path. These features can cooperate to decrease the likelihood of inadvertent removal of the surgical wire from the working aperture of the base 1930.

Figure 25:
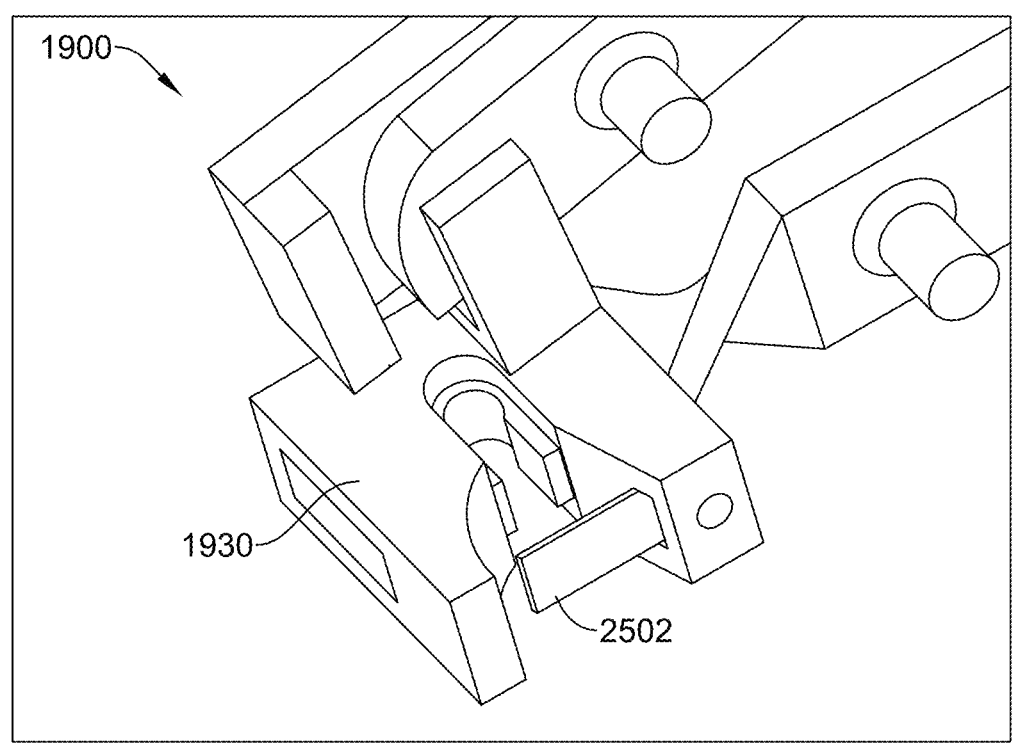
FIG. 25 is a schematic view of an illustrative guard in the form of a flexible arm.
Figure 26:
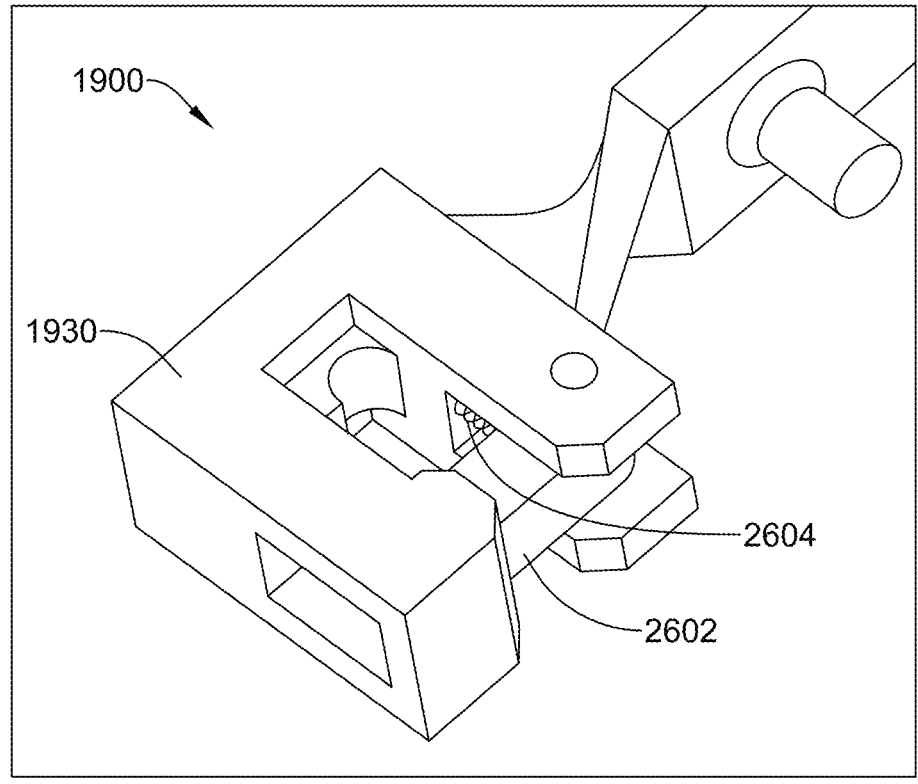
FIG. 26 is a schematic view of an illustrative guard in the form of a spring clip.
Figure 27:
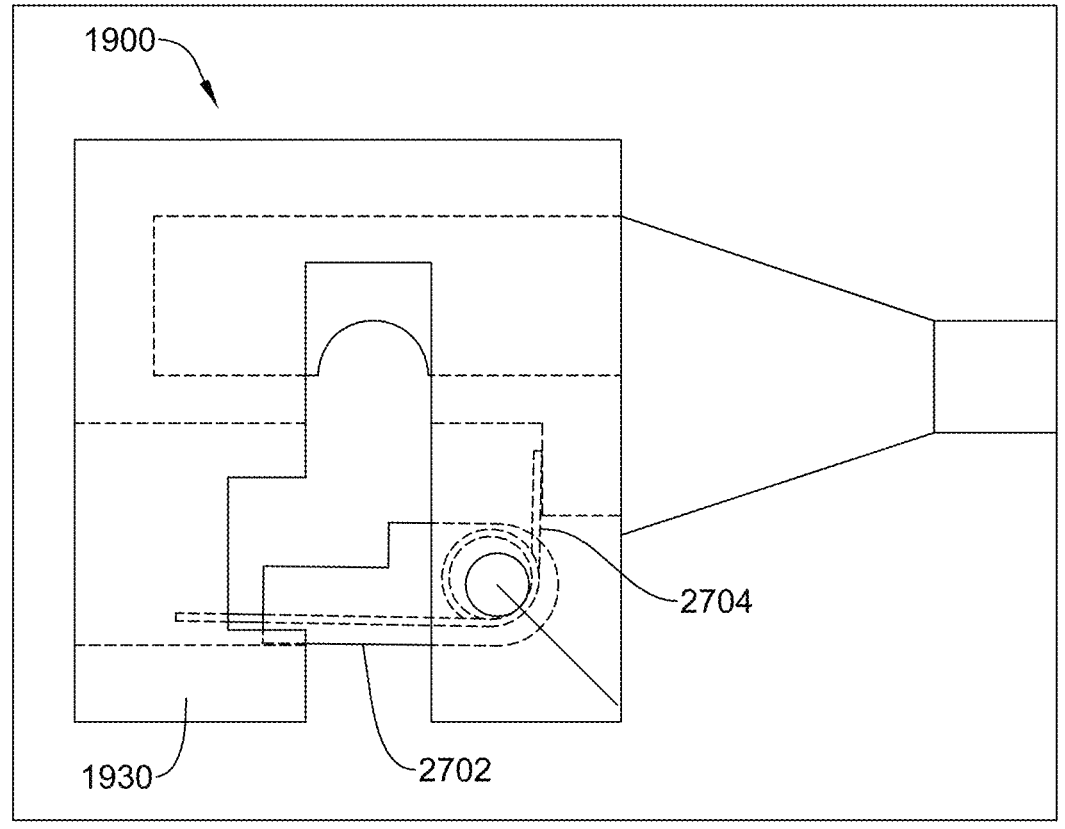
FIG. 27 is a schematic view of an illustrative guard in the form of a spring clip having a torsion spring that biases the guard closed.

FIGS. 25-27 illustrative configurations of guards for removers 1900.

FIG. 25 illustrates an example guard 2502 in the form of a flexible arm that is pinned in place and which bends out of the way from the force of a surgical wire being pushed through. In an example, the flexible arm is constructed from spring steel. The stiffness of the guard 2502 can be selected to make inadvertent removal of the surgical wire difficult while still permitting relatively easy (albeit deliberate) insertion of the surgical wire.

FIG. 26 illustrates an example guard 2602 in the form of a spring clip (e.g., as may be found in a carabiner). A spring 2604 (e.g., a compression spring or other suitable spring) biases the guard 2602 into a closed position. Advantageously this configuration can permit the lateral insertion of a surgical wire into the base 1930 by pressing the surgical wire against the guard 2602, but effectively prevents lateral removal of the surgical wire. In an example, lateral removal is difficult and instead axial removal of the surgical wire would be used.

FIG. 27 illustrates an example guard 2702 in the form of a spring clip having a spring 2704 that biases the guard 2702 closed. The guard 2702 is similar to the guard 2602, but with having a torsion spring 2704 with one arm going through the arm of the guard 2702. The other arm of the spring 2704 sits against a surface at approximately a ninety-degree angle to the guard 2702 resting position.

A wire remover can be coupled to or integrated with a retractor blade in any of a variety of ways.

Figure 28:
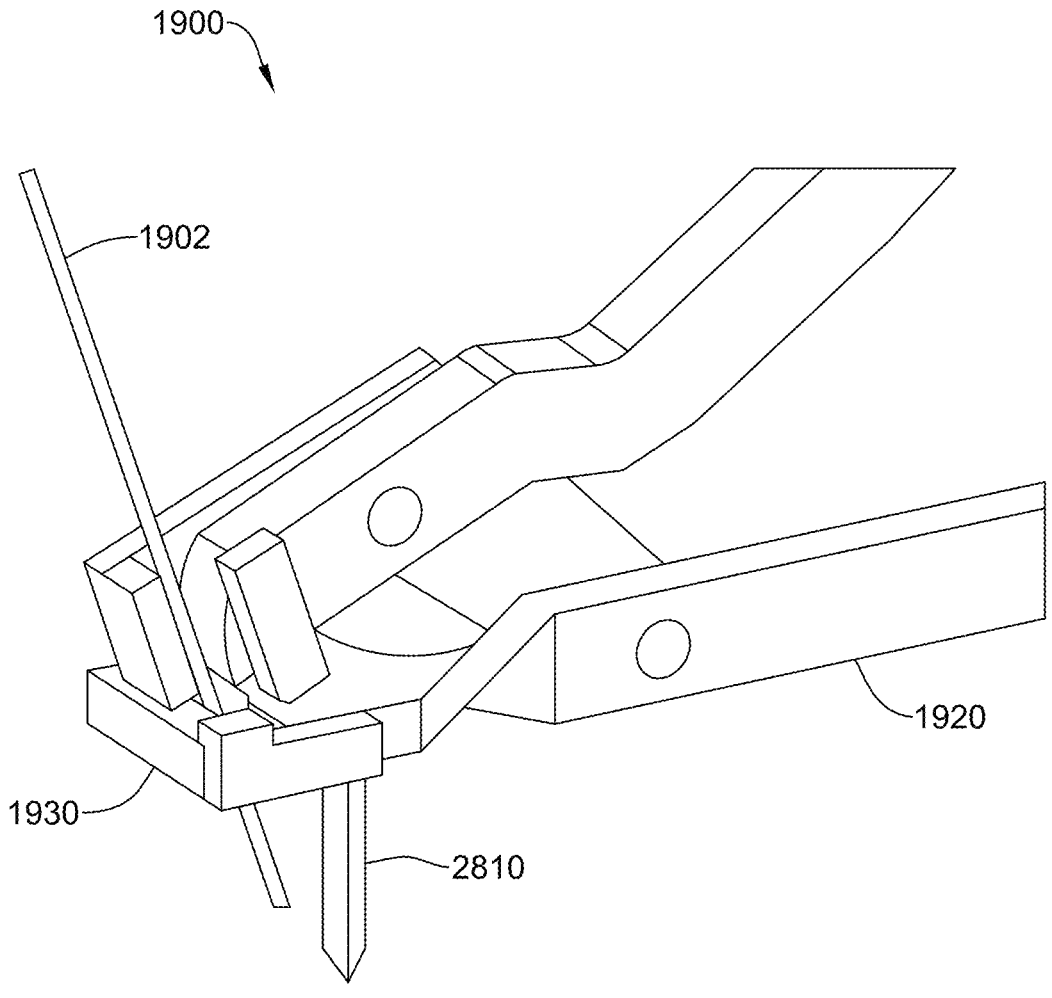
FIG. 28 is a schematic view of an illustrative integration of a remover with a retractor.

FIG. 28 an illustrative configuration of the remover 1900 configured to be integrated with a retractor (e.g., a retractor as discussed herein or other suitable retractor). Here, the remover 1900 includes an extension 2810 configured to interact with a retractor. The extension 2810 is a component extending from the base 1930 or bottom arm 1920 of the remover 1900. For example, the medial blade arm of the retractor can include a slot configured to receive one or more components (typically a supplemental blade assembly as described in U.S. Pat. No. 9,138,217, which is hereby incorporated by reference in its entirety for any and all purposes). The extension 2810 can be configured to fit into the slot and hold the remover 1900 relative to the retractor. In addition or instead, the extension 2810 can be configured in size or shape to slide into an accessory slot of a medial retractor blade of a retractor. For example, the accessory slot can traditionally be configured to receive a light cable or shim, but can be used here instead to retain the remover 1900 with respect to the retractor. Here, the extension 2810 can be sized to fit into the accessory slot and, for example, latch into grooves along the retractor blade.

In some examples, the remover 1900 has its own base 1930 and bottom arm 1920. In other examples, the retractor arm acts as one or both of the base and bottom arm. In some examples, where the remover 1900 is configured to couple with the retractor having an arm acting as one or both of the base and the bottom arm, the remover 1900 may still have a base 1930 but the base 1930 may be smaller or configured to fit around the retractor arm or blade.

In some examples, the retractor (e.g., an arm thereof) may include a connector for connecting to an articulating arm to improve stability of the retractor. For example, the connector may be what is referred to as a "poker chip" connector or may take other forms. The remover 1900 may be configured to couple with the articulating arm connector of the retractor so as to provide a stable connection between the remover 1900 and the retractor.

Figure 29:
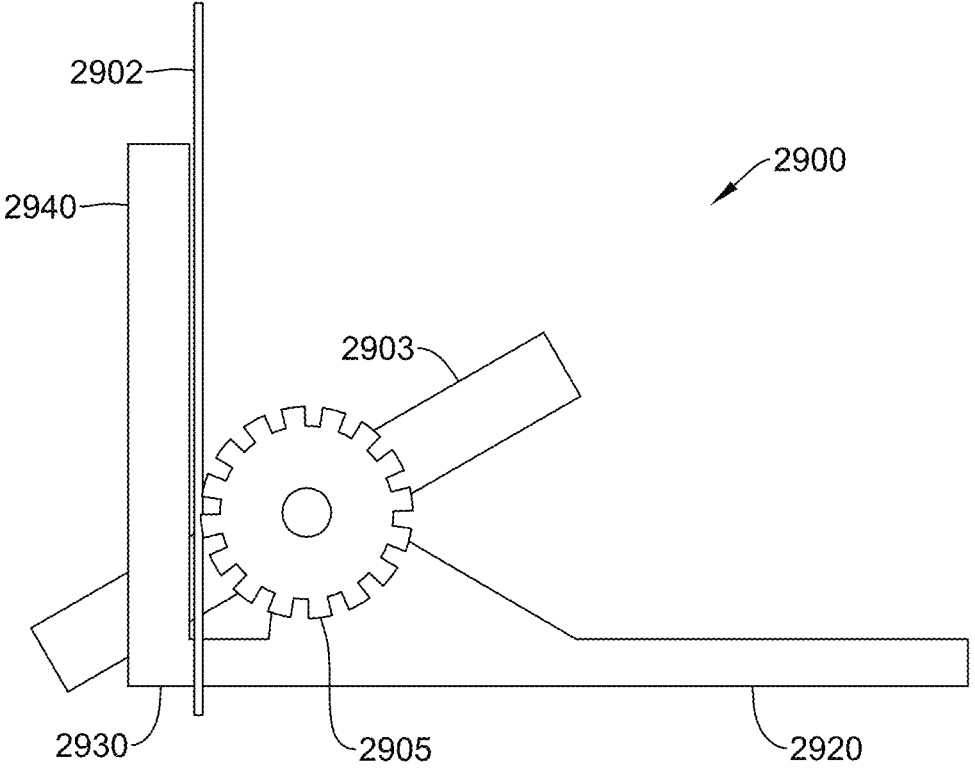
FIG. 29 is a schematic view of an illustrative remover configured to interact with a wire via a gear.

FIG. 29 illustrates an example remover 2900 configured to interact with the wire 2902 via a gear 2905. The wire 2902 is disposed between a plate 2940 and the gear 2905. As the gear 2905 is rotated by actuation of a handle 2903, the teeth of the gear 2905 bite into the wire 2902 and push the wire 2902 upward to remove it. In some examples, the gear 2905 is movable relative to the plate 2940 to aid in insertion of the wire 2902 while improving the ability of the gear 2905 to grip the wire 2902. In some examples, the gear 2905 is coupled to a second arm 2920 having or coupled to a base 2930, such that movement of the arm 2920 controls the distance between the plate 2940 and the gear 2905 and that gripping the arms 2920 together urges the gear 2905 toward the plate 2940 to grip the wire 2902.

Figure 30:
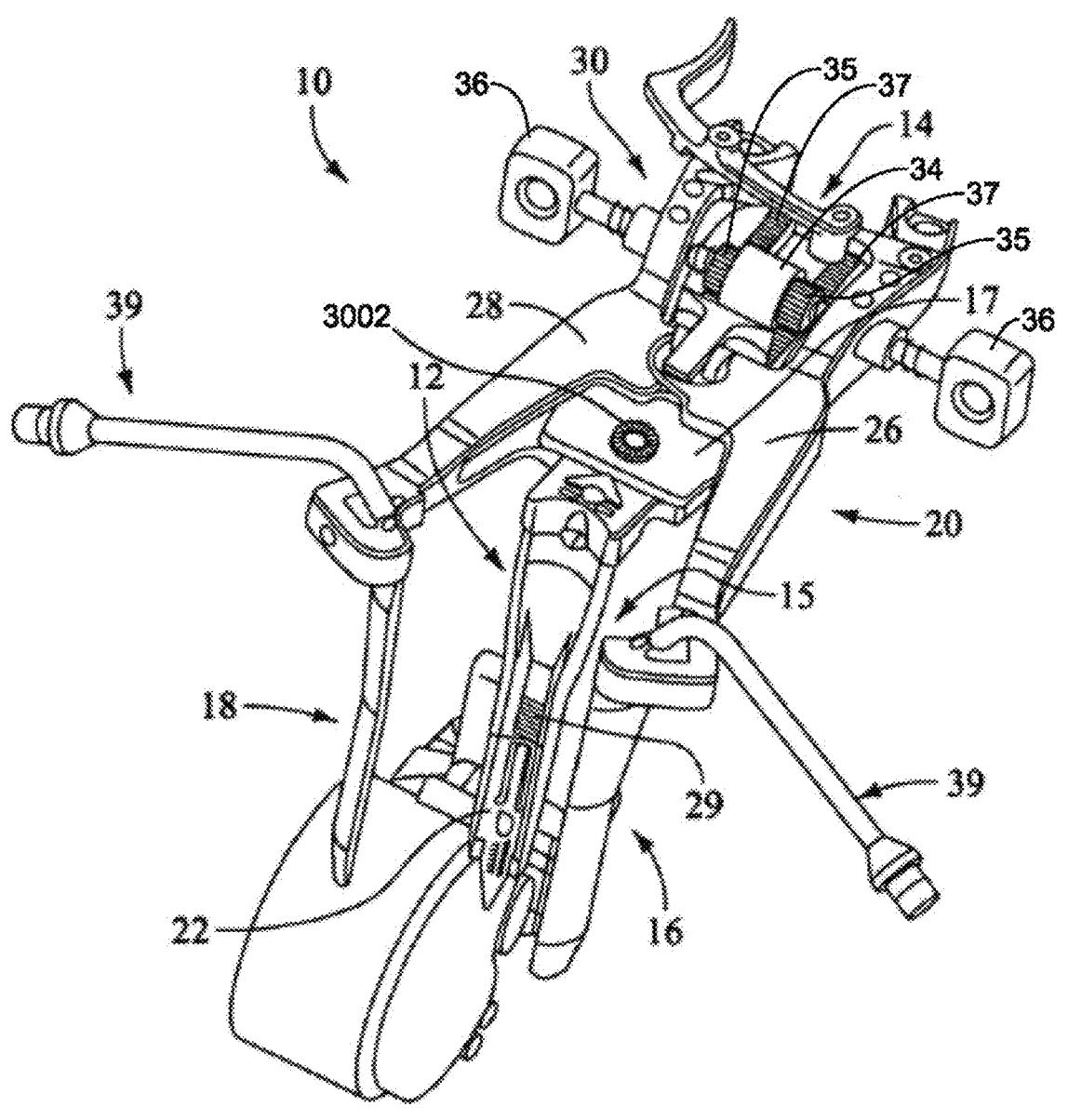
FIG. 30 is a schematic view of an illustrative tissue retraction assembly forming part of a surgical access system.

FIG. 30 illustrates a tissue retractor or retraction assembly 10 forming part of a surgical access system that can benefit from aspects disclosed herein. The retraction assembly 10 includes a plurality of retractor blades extending from a handle assembly 20. By way of example only, the handle assembly 20 is provided with a first retractor blade 12, a second retractor blade 16, and a third retractor blade 18. One or more of the retractor blades 12, 16, 18 can include one or more aspects of the retractor blades 100, 800 described elsewhere herein or of other suitable retractor blades. The retractor assembly 10 is shown in a fully retracted or "open" configuration, with the retractor blades 12, 16, 18 positioned a distance from one another so as to form an operative corridor 15 there between and extending to a surgical target site (e.g. an annulus of an intervertebral disc). Although shown and described below with regard to the three-bladed configuration, it is to be readily appreciated that the number of retractor blades may be increased or decreased without departing from the scope of the present invention. Moreover, although described and shown herein with reference to a generally lateral approach to a spinal surgical target site (with the first blade 12 being the "posterior" blade, the second blade 16 being the "cephalad-most" blade, and the third blade 18 being the "caudal-most" blade), it will be appreciated that the retractor assembly 10 of the present invention may find use in any number of different surgical approaches, including generally posterior, generally postero-lateral, generally anterior, and generally antero-lateral.

The retractor blades 12, 16, 18 may be equipped with various additional features or components. By way of example only, posterior retractor blade 12 may be equipped with a shim 22. Shim element 22 serves to distract the adjacent vertebral bodies (thereby restoring disc height), helps secure the retractor assembly 10 relative to the surgical target site, and forms a protective barrier to prevent the ingress or egress of instruments or biological structures (i.e. nerves, vasculature, etc. . . . ) into or out of the operative corridor. Each of the remaining retractor blades (cephalad-most blade 16 and caudal-most blade 18) may be equipped with a retractor extender, such as the narrow retractor extender.

Any or all of the retractor blades 12, 16, 18, the shim element 22, and/or the retractor extenders 24/25 may be provided with one or more electrodes 39 (preferably at their distal regions) equipped for use with a nerve surveillance system, such as NVM5 provided by NUVASIVE, INC. Each of the shim element 22 and/or the retractor extenders may also be equipped with a mechanism to selectively and releasably engage with the respective retractor blades 12, 16, 18. By way of example only, this may be accomplished by configuring the shim element 22 and/or the retractor extenders with a tab element capable of engaging with corresponding ratchet-like grooves 29 along the inner-facing surfaces of the retractor blades 12, 16, 18. Each of the shim element 22 and/or the retractor extenders is provided with a pair of engagement elements having, by way of example only, a generally dove-tailed cross-sectional shape. The engagement elements are dimensioned to engage with receiving portions on the respective retractor blades 12, 16, 18. In an example configuration, each of the shim element 22 and/or the retractor extenders are provided with an elongate slot for engagement with an insertion tool (not shown). Each tab member is also equipped with an enlarged tooth element which engages within corresponding grooves 29 provided along the inner surface of the retractor blades 12, 16, 18.

The handle assembly 20 may be coupled to any number of mechanisms for rigidly registering the handle assembly 20 in fixed relation to the operative site, such as through the use of an articulating arm mounted to the operating table. The handle assembly 20 includes first and second arm members 26, 28 hingedly coupled via coupling mechanism 30. The cephalad-most retractor blade 16 is rigidly coupled (generally perpendicularly) to the end of the first arm member 26. The caudal-most retractor blade 18 is rigidly coupled (generally perpendicularly) to the end of the second arm member 28. The posterior retractor blade 12 is rigidly coupled (generally perpendicularly to) a translating member 17, which is coupled to the handle assembly 20 via a linkage assembly shown generally at 14. The linkage assembly 14 includes a roller member 34 having a pair of manual knob members 36 which, when rotated via manual actuation by a user, causes teeth 35 on the roller member 34 to engage within ratchet-like grooves 37 in the translating member 17. Thus, manual operation of the knobs 36 causes the translating member 17 to move relative to the first and second arm members 26, 28.

As further illustrated, the medial arm or translating member 17 of the retractor assembly 10 has an articulating arm connector 3002.

Figure 31:
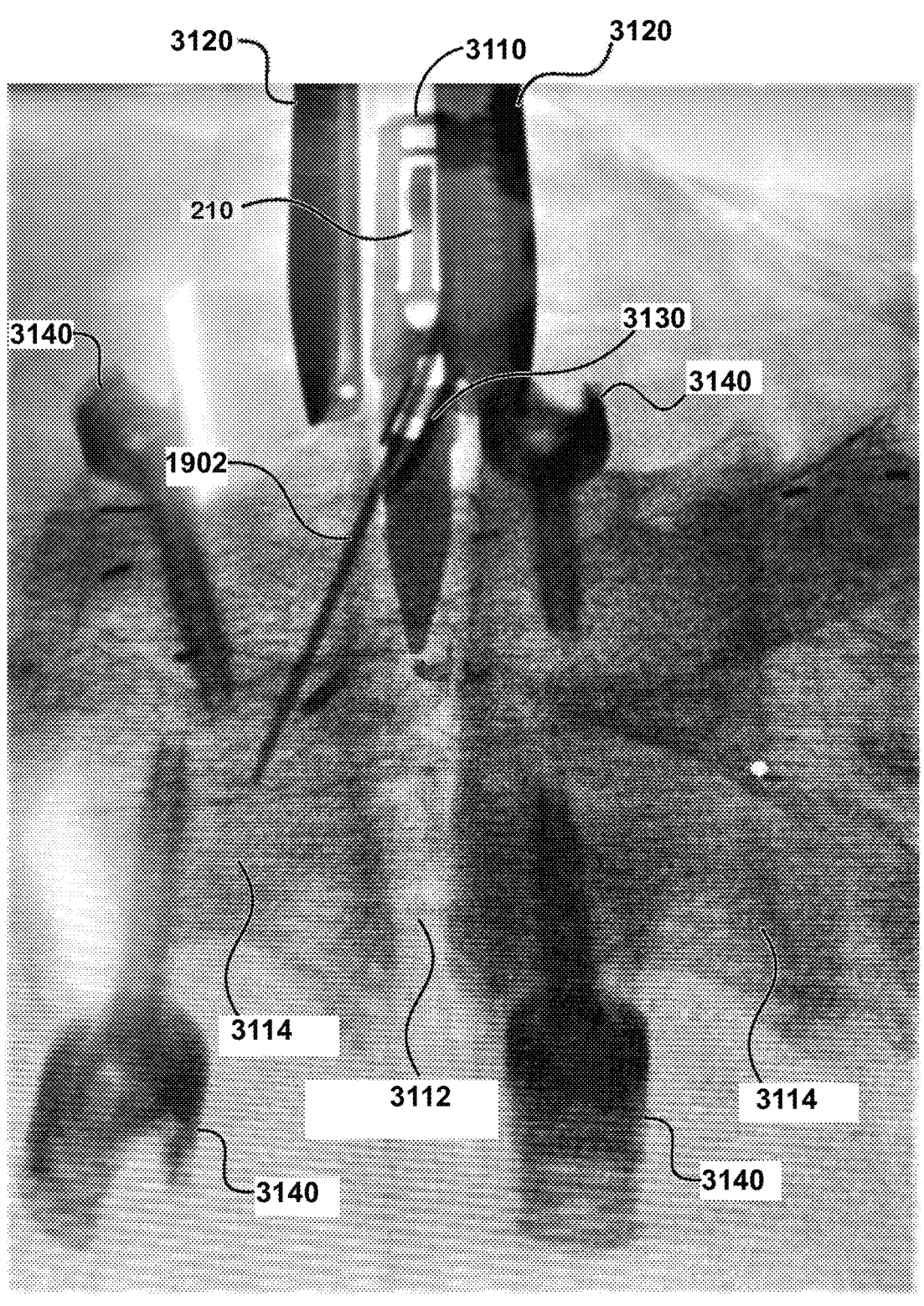
FIG. 31 schematic a radiographic image of an illustrative implanted surgical wire that can be removed using any remover feature described herein.

FIG. 31 illustrates a radiographic image of an example implanted surgical wire 1902 that can be removed using any remover feature described herein. As illustrated, a shim 3110 is disposed in intervertebral disc space 3112 between adjacent vertebrae 3114. The shim 3110 is coupled to a substantially radiolucent medial retractor blade between adjacent additional retractor blades 3120. The surgical wire 1902 is guided through the guide 3130 and into a vertebral endplate of an adjacent vertebra 3114. Bone anchors 3140 are anchored into the vertebrae and are visible herein.

Although certain embodiments and examples are provided in the foregoing description, the inventive subject matter extends beyond the specifically disclosed embodiments to other alternative embodiments and/or uses, and to modifications and equivalents thereof. Thus, the scope of the claims appended hereto is not limited by any of the particular embodiments described herein. For example, in any method disclosed herein, the operations may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the systems, and/or devices described herein may be embodied as integrated components or as separate components.

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated.

What is claimed is:

1. A retractor blade for creating an operating corridor to an operative site comprising:
    a body having a proximal end and a distal end, wherein the proximal end of the body is further away from the operative site than the distal end of the body; and
    a surgical wire path beginning proximate the proximal end of the body and ending proximate the distal end of the body,
    wherein the surgical wire path comprises a first opening in communication with the surgical wire path, the first opening is proximate the proximal end of the body and a second opening in communication with the surgical wire path, the second opening is proximate the distal end of the body,
    wherein the surgical wire path comprises a first surgical wire path and a second surgical wire path,
    wherein the first surgical wire path and the second surgical wire path converge and meet proximate the distal end of the body, and
    wherein the first surgical path and the second surgical path both exit the body at a same distal opening at the distal end of the body,
    wherein the first surgical wire path and the second surgical wire path have a first portion in which the first surgical wire path and the second surgical wire path are parallel and a second portion in which the first surgical wire path and the second surgical wire path converge toward one another.

2. The retractor blade of claim 1, wherein the surgical wire path has a first section in which the surgical wire path is parallel to a midline of the body, a second section in which the surgical wire path is angled toward the midline of the body, a third section in which the surgical wire path is angled toward the midline of the body, and a fourth section in which the surgical wire path is angled toward the midline of the body.

3. The retractor blade of claim 2, wherein the surgical wire path is straight in the first section and the second section and the surgical wire path is curved in the third section.

4. The retractor blade of claim 1, wherein the surgical wire path has a first portion completely enclosed and a second portion formed from an open channel.

5. The retractor blade of claim 1, wherein the body defines the surgical wire path.

6. The retractor blade of claim 1, further comprising:
    a tube defining the surgical wire path,
    wherein the tube extends along the body from a location proximate the proximal end of the body to a location proximate the distal end of the body.

7. The retractor blade of claim 6, wherein the tube is sunk into a face of the body.

8. The retractor blade of claim 6, wherein the tube comprises a first tube and a second tube spaced distally from the first tube.

9. The retractor blade of claim 8, wherein the first tube is straight and the second tube is curved.

10. A system comprising:
    a retractor comprising a retractor blade, wherein the retractor blade has a proximal end and a distal end and the proximal end of the retractor blade is configured to couple to the retractor;
    a surgical wire path extending along the retractor blade, the surgical wire path having a proximal opening proximate the proximal end of the retractor blade and a distal opening proximate the distal end of the retractor blade; and
    a surgical wire configured to extend along the surgical wire path from the proximal opening to the distal opening,
    wherein the surgical wire path comprises a first surgical wire path and a second surgical wire path,
    wherein the first surgical wire path and the second surgical wire path converge and meet proximate the distal end of the body, and
    wherein the first surgical path and the second surgical path both exit the body at a same distal opening at the distal end of the body,
    wherein the surgical wire path is defined by:
    a full enclosure in a first section; and
    an open channel in a second section.

11. The system of claim 10, wherein the surgical wire path is defined by a tube extending along the retractor blade, the surgical wire path is configured to receive the surgical wire.

12. The system of claim 10, wherein the surgical wire path includes:
    a straight section angled toward a midline of the retractor blade; and
    a curved section angled toward the midline of the retractor blade.

13. The retractor blade of claim 1, wherein the first surgical path and the second surgical path are asymmetrical.

* * * * *